US009902998B2

(12) United States Patent
Alcaraz Asensio et al.

(10) Patent No.: US 9,902,998 B2
(45) Date of Patent: Feb. 27, 2018

(54) NON-INVASIVE DIAGNOSTIC METHOD FOR DIAGNOSING BLADDER CANCER

(71) Applicant: FINA BIOTECH, S.L., Madrid (ES)

(72) Inventors: Antonio Alcaraz Asensio, Barcelona (ES); Lourdes Mengual Brichs, Barcelona (ES); Maria Jose Ribal Caparros, Barcelona (ES); Juan José Lozano Salvatella, Barcelona (ES)

(73) Assignee: FINA BIOTECH, S.L., Madrid (ES)

( * ) Notice: Subject to any disclaimer, the term of this patent is extended or adjusted under 35 U.S.C. 154(b) by 0 days.

(21) Appl. No.: 14/765,271

(22) PCT Filed: Jan. 31, 2014

(86) PCT No.: PCT/EP2014/051939
§ 371 (c)(1),
(2) Date: Jul. 31, 2015

(87) PCT Pub. No.: WO2014/118334
PCT Pub. Date: Aug. 7, 2014

(65) Prior Publication Data
US 2016/0017433 A1 Jan. 21, 2016

(30) Foreign Application Priority Data
Jan. 31, 2013 (EP) ..................................... 13382030

(51) Int. Cl.
*C12Q 1/68* (2006.01)
*A61B 17/00* (2006.01)
*A61B 17/32* (2006.01)
*A61B 18/12* (2006.01)

(52) U.S. Cl.
CPC ...... *C12Q 1/6886* (2013.01); *A61B 17/00234* (2013.01); *A61B 17/320016* (2013.01); *A61B 18/12* (2013.01); *A61B 2017/00278* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 5,512,437 A | 4/1996 | Gaugler et al. | |
| 2010/0086932 A1* | 4/2010 | Alcaraz Asensio .. | C12Q 1/6886 435/6.14 |

FOREIGN PATENT DOCUMENTS

| WO | 2008/113870 A1 | 9/2008 |
| WO | 2008/119858 A1 | 10/2008 |
| WO | 2013/158972 A1 | 10/2013 |

OTHER PUBLICATIONS

Aaboe M, "Gene expression profiling of noninvasive primary urothelial tumours using microarrays," Br J Cancer, vol. 93, 2005, pp. 1182-1190.
Bastacky S, et al., "The Accuracy of Urinary Cytology in Daily Practice," Cancer, vol. 87, 1999, pp. 118-128.
Boyle P., et al., "Cancer incidence and mortality in Europe, 2004," Ann Oncol, 2005, vol. 16, 2004, pp. 481-488.
Cheng L, et al., "Substaging of T1 Bladder Carcinoma Based on the Depth of Invasion as Measured by Micrometer," Cancer, vol. 86, 1999, pp. 1035-1043.
Goeman JJ, et al., "A global test for groupsof genes: testing association with a clinical outcome," Bioinfonnatics, vol. 20, 2004, pp. 93-99.
Izquierdo L, et al., "Molecular characterization of upper urinary tract tumours," BJU International, 2010; 106 (6), 868-872.
Jones JS, "DNA-based Molecular Cytology for Bladder Cancer Surveillance," Urology, vol. 67, 2006, pp. 35-45.
Jordan Am, et al., "Transitional Cell Neoplasms of the Urinary Bladder: Can Biologic Potential be Predicted from Histologic Grading?" Cancer, vol. 60, 1987, pp. 2766-2774.
Lopez-Beltran A, et al., "Tumours of the Urinary System" IARC Press Article "Tumours of the Urinary System", 2004, pp. 89-157.
Ma Ming, et al., "Expression of MAGE genes and MAGE gene products in human renal and urinary bladder tumor," Journal of Peking University, Health Sciences, 2004; 36 (2); 159-163.
Mengual L, et al., "Partially Degraded RNA from Bladder Washing is a Suitable Sample for Studying Gene Expression Profiles in Bladder Cancer," Eur Ural, 50(6); 1347-56, 2006.
Mengual L, et al., "Multiplex preamplification of specific cDNA targets prior to gene expression analysis byTaqMan Arrays," BMC Research Notes, 1:21, 2008.
Mengual L, et al., "DNA Microarray Expression Profiling of Bladder Cancer Allows Identification of Noninvasive Diagnostic Markers," J Urol, 182:741-8, 2009.
Mengual L, et al., "Gene Expression Signature in Urine for Diagnosing and Assessing Aggressiveness of Bladder Urothelial Carcinoma," Clinical Cancer Research 2010; 16 (9); 2624-2633.
Mengual L, et al., "Validation Study of a Noninvasive Urine Test for Diagnosis and Prognosis Assessment of Bladder Cancer: Evidence for Improved Models," The Journal of Urology, 2013; 191 (1); 261-269.
Miceli F, et al., "Expression and subcellular localization of CRH and its receptors in human endometrial cancer," Molecular and Cellular Endocrinology, Elsevier Ireland LTD., 2009.
Pansadoro V, et al., "Bacillus Calmette-Guerin in the Treatment of Stage T1 Grade 3 Transitional Cell Carcinoma of the Bladder: Long-Term Results," J Urol, vol. 154, 1995, pp. 2054-2058.

(Continued)

*Primary Examiner* — Antonio Galisteo Gonzalez
(74) *Attorney, Agent, or Firm* — Knobbe, Martens, Olson & Bear, LLP

(57) ABSTRACT

Non-invasive diagnostic methods for diagnosing bladder cancer are based on determining the expression level of one or more markers. The one of the markers comprises the IGF2 gene in a sample from the subject to be studied. Other suitable markers include MAGEA3, ANXAIO, AHNAK2, CTSE, CRH, KLF9, KRT20, POSTN, PPP1R14D, SLCIA6, TERT, ASAM, MCMIO, EBF1, CFH and MMP12 and possibly FOXM1, KIF20A, MELK, CDK1.

6 Claims, 2 Drawing Sheets

(56) References Cited

OTHER PUBLICATIONS

Pignot G, et al., "Hedgehog pathway activation in human transitional cell carcinoma of the bladder," British Journal of Cancer, 2012; 106, 1177-1186.
Robin X, et al., "pROC: An Open-Source Package for R and S+ to Analyze and Compare ROC Curves," BMC Bioinformatics, vol. 12, 2011, pp. 77.
Sanchez-Carbayo M, et al., "Molecular Profiling of Bladder Cancer Using cDNA Microarrays: Defining Histogenesis and Biological Phenotypes," Cancer Res, vol. 62, 2002, pp. 6973-6980.
Sanchez-Carbayo M, et al., "Defining Molecular Profiles of Poor Outcome in Patients With Invasive Bladder Cancer Using Oligonucleotide Microarrays," J Clin Oncol,vol. 24, 2006, pp. 778-789.
Takata R, et al., "Predicting Response to Methotrexate, Vinblastine, Doxorubicin, and Cisplatin Neoadjuvant Chemotherapy for Bladder Cancers through Genome-Wide Gene Expression Profiling," Clin Cancer Res, vol. 11, 2005, pp. 2625-2636.
Thykjaer T, et al., "Identificationof Gene Expression Patterns in Superficial and Invasive Human Bladder Cancer," Cancer Res, vol. 61, 2001, pp. 2492-2499.
Watson J A, et al., "Urinary insulin-like growth factor 2 identifies the presence of urothelial carcinoma of the bladder," BJU International, 2009; 103 (5); 694-697.
International Search Report dated Apr. 14, 2014 for PCT/EP2014/051939.
Ribal, M.J., et al., Gene expression test for the non-invasive diagnosis of bladder cancer: A prospective, blinded international multi center validation study, European Journal Cancer, vol. 54, pp. 131-138, 2016.

\* cited by examiner

| | N T/h C | SN | SP | PPV | NPV |
|---|---|---|---|---|---|
| Training cohort | 97/114 | 86 | 93 | 91 | 88 |
| Validation cohort | 96/111 | 80 | 86 | 84 | 83 |

NON-INVASIVE DIAGNOSTIC METHOD FOR DIAGNOSING BLADDER CANCER

CROSS REFERENCE TO RELATED APPLICATIONS

This application is the U.S. National Phase of International Application No. PCT/EP2014/051939, filed Jan. 31, 2014, designating the U.S. and published in English as WO 2014/118334 on Aug. 7, 2014 which claims the benefit of European Patent Application No. 13382030.8, filed Jan. 31, 2013.

TECHNICAL FIELD OF THE INVENTION

The field of application of the present invention is in the health sector, primarily in the fields of "Oncological Urology" and "Molecular Biology". Specifically, the invention relates to non-invasive diagnostic methods for diagnosing bladder cancer.

BACKGROUND OF THE INVENTION

Urothelial carcinoma (UC) of the bladder is the seventh most common malignant tumor worldwide among men, with an approximate number of 350.000 new cases diagnosed per year. UC is the fourth cause of death due to neoplasm and is the second most common tumor of the urinary system after prostate cancer and with it, due to its high relapse rate, is the main cause of uro-oncological attention (Boyle P., Ferlay J. Cancer incidence and mortality in Europe, 2004. Ann Oncol 2005; 16:481-8).

More than 90% of cases of UC of the bladder are transitional cell carcinomas, although they can also present as adenocarcinomas and squamous cell carcinomas. The transitional cell epithelium is located in the inner layer of the urothelial mucosa and is separated from the muscle layer by the lamina propria. Approximately 75-80% of the cases of UC are superficial tumors, i.e., they do not invade the muscle layer, so they are called non muscle-invasive bladder cancer (NMIBC). 70-80% of them are confined only to the urothelial mucosa (Ta and CIS stage), whereas 20-30% reach the lamina propria (T1 stage) without invading the muscle layer of the bladder wall (Cheng L, Weaver A L, Neumann R M, Scherer B G, Bostwick D G. Substaging of T1 bladder carcinoma based on the depth of invasion as measured by micrometer: A new proposal. Cancer 1999; 86:1035-43). NMIBCs are characterized by their multiplicity, their tendency to relapse and their good prognosis. The survival rate of NMIBC patients is 90% at 5 years and 80% at 10 years (Pansadoro V, Emilliozzi P, Defidio L, et al. *Bacillus* Calmette-Guerin in the treatment of stage T1 grade 3 transitional cell carcinoma of the bladder: long-term results. J Urol 1995; 154:2054-8). While the risk of recurrence in these patients is approximately 70%, only 10-15% progress to muscle-invasive bladder cancer (MIBC). A close association between the tumor grade and the risk of tumor progression has been observed (Jordan A M, Weingarten J, Murphy W M. Transitional cell neoplasms of the urinary bladder. Can biologic potential be predicted from histologic grading? Cancer 1987; 60:2766-74). Most Ta tumors are low grade tumors. These tumors frequently return but less than 5% progress. On the other hand, many T1 tumors are high grade tumors and 30-50% progress to muscle layer-infiltrating tumors. In contrast, approximately 20% of the cases of UC present as MIBC at the time of diagnosis. These are aggressive tumors that lead to death in 2 years if they are not treated. 50% of MIBC patients die after 2 years due to distant metastasis or local relapse despite receiving radical surgical treatment. The basic problem of MIBC lies in the brevity of its pre-invasive step, which conditions that when the clinical phase is reached, 27-60% of the cases have already affected the deep muscle layer, 25% reach the prevesical fat and 14% have clinically detectable distant metastases.

Current diagnostic systems are based on a combination of urinary cytology (from desquamated cells in the urine) and the direct observation of the bladder by means of cystoscopy. Cystoscopy is in fact the main tumor diagnostic and follow-up technique. It is performed by transurethral route, so it is an invasive and rather bothersome technique for patients. The sensitivity and specificity of this technique were thought to be rather high, although improvements in the technique itself (fluorescent cystoscopy) indicate that this is probably not the case and that part of the recurrence observed in superficial tumors could be due to the lack of total resection of non-visible parts thereof (Jones J S. DNA-based molecular cytology for bladder cancer surveillance. Urology 2006; 67:35-45). Furthermore, the interpretation of the cytology is highly dependent on the observer, therefore there can be inter-observer differences, especially in low grade tumors.

Advancement in knowledge about molecular events leading to UC progression has stimulated the study of gene expression profiling by means of DNA microarrays using RNA obtained from different classes of UC, including non-muscle and muscle-invasive tumors (Bastacky S, Ibrahim S, Wilczynski S P, Murphy W M. The accuracy of urinary cytology in daily practice. Cancer 1999; 87:118-28; aboe M, Marcussen N, Jensen K M, Thykjaer T, Dyrskjot L, Orntoft T F. Gene expression profiling of noninvasive primary urothelial tumours using microarrays. Br J Cancer 2005; 93:1182-90; Thykjaer T, Workman C, Kruhoffer M, et al. Identification of gene expression patterns in superficial and invasive human bladder cancer. Cancer Res 2001; 61:2492-9), different stages of UC progression (Sanchez-Carbayo M, Socci N D, Charytonowicz E, et al. Molecular profiling of bladder cancer using cDNA microarrays: defining histogenesis and biological phenotypes. Cancer Res 2002; 62:6973-80) and in patients with a different clinical progression (Sanchez-Carbayo M, Socci N D, Lozano J, Saint F, Cordon-Cardo C. Defining molecular profiles of poor outcome in patients with invasive bladder cancer using oligonucleotide microarrays. J Clin Oncol 2006; 24:778-89). The same approach has also been used for the identification of a panel of 14 predictive genes which separate UC-responding patients from non UC-responding patients with respect to different therapeutic agents (Takata R, Katagiri T, Kanehira M, et al. Predicting response to methotrexate, vinblastine, doxorubicin, and cisplatin neoadjuvant chemotherapy for bladder cancers through genome-wide gene expression profiling. Clin Cancer Res 2005; 11:2625-36).

Although direct urothelial tissue analysis is the most comfortable alternative, to develop a routine diagnostic method it would be of great interest that it is not invasive because invasive maneuvers reduce the patients' quality of life and represent a much larger economic health burden. Blood, and particularly urine which is in contact with the entire bladder epithelium, and therefore with the tumor mass, are suitable sources of biological material for the detection of tumor markers, given that they represent an easy and non-invasive way of obtaining the sample to be analyzed.

A considerable number of papers have focused on studying tumor markers in urine in search of a non-invasive diagnostic method for diagnosing UC of the bladder. In fact, different tests have been marketed for this purpose (NMP22, UroVysion, ImmunoCyt, Accu-Dx, etc.), but even though most of them are more sensitive than urinary cytology, the latter is still the most specific.

The identification of marker genes for bladder cancer is complex due to the heterogeneous nature of said tumors. Diagnostic methods comprising the detection of marker proteins in urine (WO 2008/119858A1) have recently been developed, though it is only useful in the diagnosis of transitional carcinoma. International patent application WO 2008/113870 describes, among others, an in vitro non-invasive method for the diagnosis and/or prognosis of bladder cancer based on the expression profile of the ANXA10, C14orf78 (AHNAK2), CTSE, CRH, IGF2, KLF9, KRT20, MAGEA3, POSTN, PPP1R14D, SLC1A6, TERT, ASAM and MCM10 genes in a bladder fluid sample; although this method has high sensitivity and specificity, its use requires analyzing 14 markers, which increases the cost of the analysis and makes it very complex from a methodological viewpoint.

Despite there being some non-invasive diagnostic methods for diagnosing bladder cancer, none of them is being used routinely in clinical practice, so there is still a need to develop alternative methods for the non-invasive diagnosis of bladder cancer which allow diagnosing bladder cancer with high sensitivity and specificity and require the analysis of a smaller number of markers.

BRIEF DESCRIPTION OF THE INVENTION

In an aspect, the invention relates to an in vitro method for diagnosing if a subject suffers bladder cancer, wherein said method is that identified herein as the first method of the invention, the second method of the invention or the third method of the invention.

In another aspect, the invention relates to a method for diagnosing if a subject suffers bladder cancer, wherein said method is that identified herein as the fourth method of the invention, the fifth method of the invention or the sixth method of the invention.

In another aspect, the invention relates to a method for treating a subject who suffers bladder cancer, wherein said method is that identified herein as the seventh method of the invention, the eighth method of the invention or the ninth method of the invention.

In another aspect, the invention relates to the use of the IGF2 gene as a marker in bladder cancer diagnosis or for bladder cancer monitoring.

In another aspect, the invention relates to the use of a combination of genes comprising, or consisting of, the IGF2 gene and a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes as a marker in bladder cancer diagnosis or for bladder cancer monitoring.

In another aspect, the invention relates to the use of a combination of genes comprising the IGF2 gene and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof, with the proviso that said combination is not any of the following combinations:

ANXA10, AHNAK2, CTSE, CRH, KLF9, KRT20, MAGEA3, POSTN, PPP1R14D, SLC1A6, TERT, ASAM and MCM10;

ANXA10, AHNAK2, CTSE, CRH, KLF9, KRT20, MAGEA3, POSTN, PPP1R14D, SLC1A6 and TERT;

ANXA10, CRH, KRT20, MAGEA3, POSTN, SLC1A6 and TERT;

ANXA10, CTSE, CRH, KRT20, MAGEA3, SLC1A6, TERT and MCM10; or

ANXA10, CTSE, CRH, KRT20, MAGEA3, SLC1A6 and TERT;

as a marker in bladder cancer diagnosis or for bladder cancer monitoring.

In another aspect, the invention relates to a kit, wherein said kit is that identified herein as the first kit of the invention, the second kit of the invention or the third kit of the invention.

In another aspect, the invention relates to the use of said kits provided by the present invention for bladder cancer diagnosis or for bladder cancer monitoring.

DETAILED DESCRIPTION OF THE INVENTION

Figure 1:
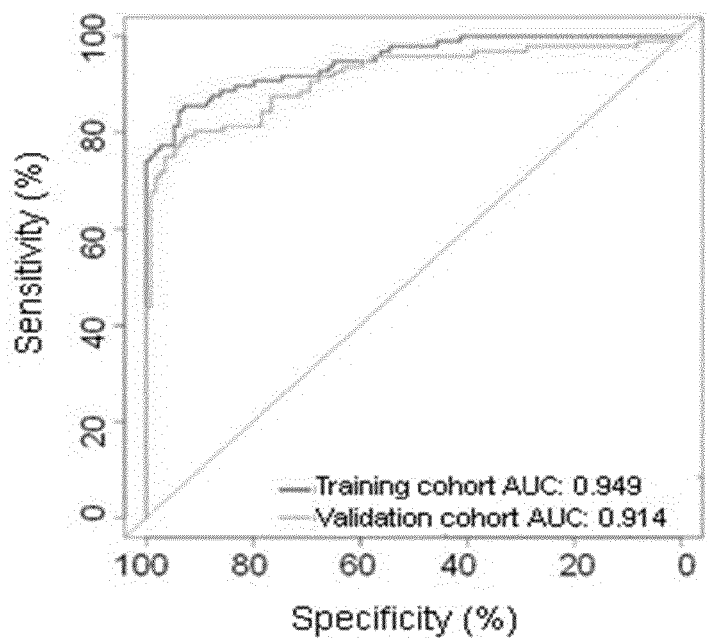
FIG. 1: Diagnostic performance of the 12-gene model (A) ROC curve for the 12-gene model in the training cohort (n=211) and in the validation cohort (n=207). Cut-off: 0.525. (B) 12-gene model sensitivity in different risk groups in the validation set samples (the Ta Gx and Tx LG samples were excluded from this analysis).
Figure 1:
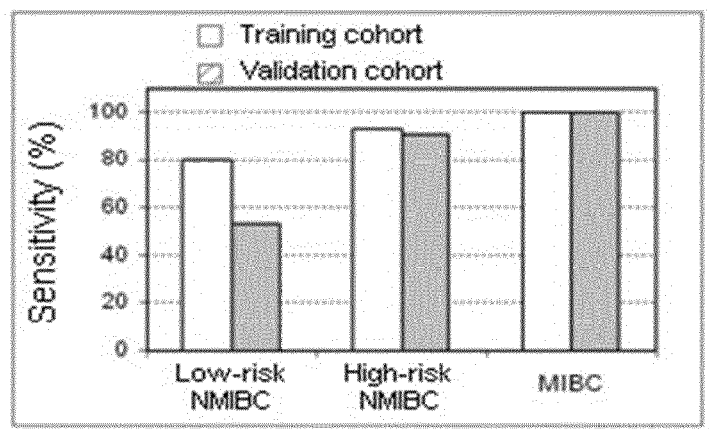
Figure 2:
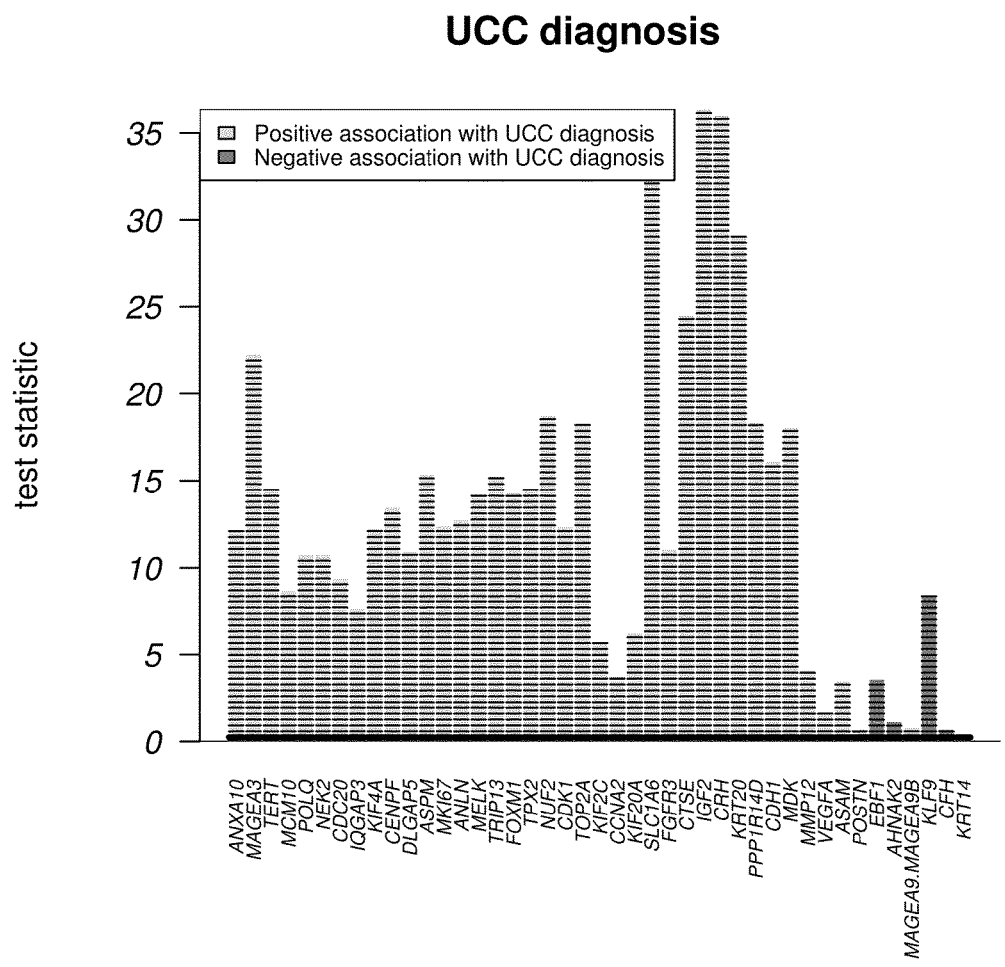
FIG. 2: Bar chart showing the influence of each gene studied in UC diagnosis. The bars exceeding the reference lines correspond to a statistically significant association (p<0.05). Darker bars represent the negative association (EBF1, AHNAK2, MAGEA9.MAGEA9B, KLF9, CRH and KRT14), whereas clearer bars represent the positive association. The selection of genes from the genetic signatures of UC diagnosis for the most part coincides with the genes having bars representing a higher influence.

The authors of the present invention have developed an in vitro non-invasive method for bladder cancer diagnosis based on determining the expression levels of one or more genes acting as genetic markers.

Methods of the Invention

The authors of the present invention have observed that the IGF2 gene is a good marker for bladder cancer diagnosis. This finding allows determining the bladder cancer diagnosis in a subject by means of a non-invasive method based on comparing the expression level of said gene (and optionally of other genes with bladder cancer diagnostic value) in the sample from the subject under study with its reference value.

Therefore in one aspect, the invention relates to an in vitro method, hereinafter "first method of the invention", for diagnosing if a subject suffers bladder cancer, which comprises:

a) determining the expression level of the IGF2 gene in a sample from said subject; and b) comparing the expression level of said IGF2 gene in said sample with its reference value;

wherein an expression level of the IGF2 gene in the sample from the subject greater than said reference value for said gene is indicative that said subject suffers bladder cancer.

As it is used herein, the term "bladder cancer" refers to that type of cancer that begins in bladder tissue and includes any cancer classified within any of the stages according to the TNM system [Sobin L H & Wittekind C H. TNM Classification of Malignant Tumours. International Union Against Cancer., ed. 6th. New York: John Wiley & Sons; 2002], such as for example transitional cell carcinoma (also known as urothelial carcinoma or UC), squamous cell carcinoma, adenocarcinomas or small cell carcinoma. The prognosis is closely related to the results of classifying in stages:

TM: primary tumor
Ta: non-invasive papillary carcinoma or papillary carcinoma confined to the mucosa.
Tis: in situ carcinoma. Flat superficial tumor that does not invade the lamina propria.
T1: tumor that invades the sub-epithelial connective tissue or that invades the lamina propria. Tis and T1 are in turn classified as high grade, i.e., they have an enormous potential for malignancy and invasion.
T2: tumor that invades the bladder muscle layer that in turn is divided into:
  T2a: tumor that invades the superficial muscle layer or the inner half; and
  T2b: tumor that invades the deep muscle layer or the outer half.
T3: tumor that invades beyond the muscle layer or that invades the prevesical fat; in turn it is divided into:
  T3a: microscopic invasion; and
  T3b: macroscopic invasion.
T4: tumor that invades structures adjacent to the urinary bladder. It is divided into two sub-types:
  T4a: invasion of the prostate, uterus or vagina; and
  T4b: invasion of the pelvic or abdominal wall.
NX: lymph node involvement. The classification is carried out based on the number of nodes involved and on the size thereof: N0 (no lymph node involvement), N1 (involvement of a single node smaller than 2 cm), N2 (involvement of one or more nodes smaller than or equal to 5 cm) and N3 (involvement of a node larger than 5 cm).
MX: presence of metastasis. M0: no distant metastasis. M1: distant metastasis.

Bladder cancer can also be classified depending on the grade characteristics of the cancer as established by the World Health Organization (WHO). By means of this classification, it is considered that a tumor is a high grade or HG tumor if it is characterized by having a high invasive power for invading other tissues and a high malignancy, or it is considered a low grade or LG tumor when it is characterized by having a low malignant and invasiveness potential.

As it is used herein, the term "diagnose" or "diagnosis" refers to evaluating the probability according to which a subject suffers a specific pathology (in this case, bladder cancer). As the skilled in the art will understand, such evaluation may not be correct for 100% of the subjects to be diagnosed, although it preferably is. The term, however, requires being able to identify a statistically significant part of the subjects, such as the subject suffers said pathology (in this case, bladder cancer). The person skilled in the art can determine if a part is statistically significant using various well-known statistical evaluation tools, for example, by means of determining confidence intervals, determining the p-value, the Student's t-test, the Mann-Whitney test, etc. Information and details about said tools can be found in Dowdy and Wearden, Statistics for Research, John Wiley & Sons, New York 1983. Preferred confidence intervals are at least 50%, at least 60%, at least 70%, at least 80%, at least 90% or at least 95%. The p-values are preferably 0.2, 0.1, 0.05, 0.025, 0.001 or less.

As it is used herein, the term "subject" refers to any animal classified as a mammal and includes but is not restricted to domestic and farm animals, primates and humans, for example, human beings, non-human primates, cows, horses, pigs, sheep, goats, dogs, cats, or rodents. The subject is preferably a male or female human being of any age or race.

As it is used herein, the term "marker" or "marker gene" refers to a gene which is differentially expressed in populations showing different phenotypes and the differential expression of which, alone or in combination with other genes is correlated with a specific phenotype to a greater extent than what would be expected randomly.

As it is used herein, the term "sample" refers to biological material isolated from a subject and therefore includes biological samples. Said sample can contain any biological material suitable for detecting the desired marker and can comprise cells and/or non-cellular material from the subject. In general, a sample can be isolated from any suitable biological tissue or fluid; nevertheless, said sample is preferably a sample comprising bladder fluid from the subject under study for putting the present invention into practice. Said bladder fluid sample can be a urine sample, for example, a micturition urine sample, a sample of bladder wash, etc., and can be obtained by means of any conventional method.

In a first step, the first method of the invention comprises, or consists of, determining the expression level of the IGF2 gene in a sample from the subject under study. As it is used herein, the term "expression level" refers to the value of a parameter that measures the degree of expression of a specific gene. Said value can be determined by measuring the mRNA level of the gene of interest or by measuring the amount of protein encoded by said gene of interest.

As it is used herein, the term "IGF2" refers to insulin-like growth factor 2, also known as C11orf43, IGF-II, FLJ22066, FLJ44734, INSIGF or PP9974. The human IGF2 gene is located in chromosome 11 and has accession number NG 008849.1 in the GenBank database (version of 16 Jan. 2013).

Virtually any conventional method for detecting and quantifying the expression level of a gene can be used within the framework of the present invention for detecting and quantifying the expression level of a specific gene. By way of non-limiting illustration, the expression level of a gene can be determined by means of quantifying the mRNA level of said gene or by means of quantifying the level of protein encoded by said gene.

In a particular embodiment, the expression level of the IGF2 gene is determined by measuring the expression level of transcription product (mRNA) of said gene in a sample from the subject under study. For this purpose, the sample can be treated to physically or mechanically break up the structure of the tissue or cell for the purpose of releasing the intracellular components into an aqueous or organic solution to prepare the nucleic acids for additional analysis. Care is preferably taken to prevent RNA degradation during the extraction process.

In a preferred embodiment, the expression level is determined using the RNA obtained from the cells contained in a bladder fluid sample, for example urine, from the subject under study. By way of non-limiting illustration, the bladder fluid sample, for example urine, can be collected in a container suitable to that end, preferably in a container treated with RNA stabilizing agents (for example, $\frac{1}{25}$ volumes of 0.5 M EDTA, pH 8). The sample can be processed at the time it is collected or, if desired, can be stored for subsequent processing, for example, in the following 24 hours, under suitable conditions to prevent degradation of the sample. To settle the cells of the bladder fluid sample, for example urine, suitable centrifugation, for example at 1,000×g for 10 minutes at 4° C., can be carried out. The cell pellets can be processed right then or can be frozen, for example at −80° C., until the RNA is extracted. If desired, after centrifugation the cell pellets can be resuspended in agents suitable for isolating RNA, for example in Trizol (Invitrogen, Carlsbad, Calif., USA). The volume of Trizol that is added to the cell pellet could be modified depending on the initial volume of the sample. If desired, after centrifuging the sample and obtaining the cell pellet the suitable volume of Trizol, for example 1 ml for every 50 or 100 ml of bladder fluid, for example urine, can be added and the sample can be stored at −80° C. until processing is desired. The total amount of RNA obtained from a sample can be quantified by means of a spectrophotometer measuring absorbance at 260 nm (for example NanoDrop).

Methods for determining the amount of mRNA are well-known in the state of the art. For example, the nucleic acid contained in the sample, such as the bladder fluid sample from the subject under study, is extracted according to conventional methods, for example, by means of using lytic enzymes, chemical solutions or fixing resins. The extracted mRNA can be detected by hybridization (for example by means of Northern blot analysis or DNA or RNA arrays (microarrays) after converting mRNA into labeled cDNA) and/or amplification by means of a enzymatic chain reaction. In general, quantitative or semi-quantitative enzymatic amplification methods are preferred. The polymerase chain reaction (PCR) or quantitative real-time RT-PCR or semi-quantitative RT-PCR technique is particularly advantageous. Primer pairs are preferably designed for the purpose of superimposing an intron to distinguish cDNA amplification from the contamination from genomic DNA (gDNA). Additional primers or probes, which are preferably labeled, for example with fluorescence, which hybridize specifically in regions located between two exons, are optionally designed for the purpose of distinguishing cDNA amplification from the contamination from gDNA. If desired, said primers can be designed such that approximately the nucleotides comprised from the 5' end to half the total length of the primer hybridize with one of the exons of interest, and approximately the nucleotides comprised from the 3' end to half the total length of said primer hybridize with the other exon of interest. Suitable primers can be readily designed by a person skilled in the art. Other amplification methods include ligase chain reaction (LCR), transcription-mediated amplification (TMA), strand displacement amplification (SDA) and nucleic acid sequence based amplification (NASBA). The amount of mRNA is preferably measured quantitatively or semi-quantitatively. Relevant information about conventional methods for quantifying the expression level of a gene can be found, for example, in Sambrook et al., 2001 [Sambrook, J., et al., "Molecular cloning: a Laboratory Manual", 3rd ed., Cold Spring Harbor Laboratory Press, N.Y., Vol. 1-3].

In a particular embodiment, the expression level of the IGF2 gene is determined by means of real-time reverse transcription-polymerase chain reaction (RT-qPCR).

To normalize the expression values of one gene among different samples, comparing the mRNA level of the gene of interest in the samples from the subject object of study with a control RNA level is possible. As it is used herein, a "control RNA" is an RNA of a gene the expression level of which does not differ depending on if they are tumor or non-tumor cells, for example a gene that is constitutively expressed both in tumor cells and in non-tumor cells; a control RNA is preferably an mRNA derived from a housekeeping gene encoding a protein that is constitutively expressed and carrying out essential cell functions. Illustrative, non-limiting examples of housekeeping genes for use in the present invention include GUSB (beta-glucuronidase), PPIA (peptidyl-prolyl isomerase A), β-2-microglobulin, GAPDH, PSMB4 (proteasome subunit beta type-4), ubiquitin, transferrin receptor, 18-S ribosomal RNA, cyclophilin, tubulin, β-actin, 3-monooxygenase/tryptophan 5-monooxygenase tyrosine activation protein (YWHAZ), etc. In a particular embodiment, the control RNA is GUSB and/or PPIA mRNA.

On the other hand, determining the expression level of a gene of interest by means of determining the expression level of the protein encoded by said gene, because increased expression of a gene is usually accompanied by an increase in the amount of corresponding protein, is also possible. The determination of the amount of a protein corresponding to the expression of a specific gene can be performed using any conventional method for protein detection and quantification, for example by means of an immunoassay, etc. By way of non-limiting illustration, said determination can be performed using antibodies with the capability to bind specifically to the protein to be determined (or fragments thereof with the antigenic determinants) and subsequent quantification of the antigen-antibody complex derivatives. The antibodies can be, for example, polyclonal sera, hybridoma supernatants or monoclonal antibodies, fragments of antibodies, Fv, Fab, Fab' and F(ab')$_2$, scFv, diabodies, triabodies, tetrabodies, humanized antibodies, etc. Said antibodies may (or may not) be labeled with a marker. Illustrative, non-limiting examples of markers that can be used in the present invention include radioactive isotopes, enzymes, fluorophores, chemiluminescent reagents, enzyme cofactors, enzyme substrates, enzyme inhibitors, etc. There is a wide range of well-known assays that can be used in the present invention, such as, for example, assays based on Western-blot or immunoblot techniques, ELISA (enzyme-linked immunosorbent assay), RIA (radioimmunoassay), EIA (enzyme immunoassay), DAS-ELISA (double antibody sandwich ELISA), immunocytochemical or immunohistochemical techniques, etc. Other ways of detecting and quantifying the protein include affinity chromatography, ligand binding assay techniques, etc.

In the second step, the first method of the invention comprises, or consists of, comparing the expression level of the IGF2 gene in the sample from the subject under study with its reference value. The term "reference value" refers to a laboratory value used as a reference for the values/data obtained from samples obtained from the subjects. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample from the subject object of study but obtained at a previous point in time. The reference value can be based on a high number of samples, such as the values obtained in a population of the subjects of the chronological age group coinciding with that of the subject object of study or based on a set of inclusion or exclusion samples of the sample to be analyzed. The reference value can be based on the expression values of the markers to be compared obtained from samples from healthy subjects who do not have a disease state or a particular phenotype. For example, the reference value can be based on the expression level of the marker to be analyzed obtained from bladder fluid samples, for example urine, from subjects who do not have bladder cancer or who do not have a history of bladder cancer. On the other hand, the reference value can be based on the expression level of the gene to be analyzed obtained from subjects who have had a surgical resection of the tumor and have not experienced a relapse. In a preferred embodiment, the reference value is obtained from a sample or a set of samples from healthy subjects or subjects without a prior history of bladder cancer. In another preferred embodiment, the reference value is obtained from a sample or a set of samples from subjects who have had a surgical resection of a tumor in the bladder and have not experienced a relapse, preferably in the absence of adjuvant chemotherapy. The person skilled in the art will see that the type of sample can vary depending on the specific method to be performed.

Once the reference value has been established, the expression level of the IGF2 gene in the sample from the subject under study is compared with the reference value. As a consequence of this comparison, the expression level of the gene of interest (for example, IGF2 in the first method of the invention) in the sample from the subject can be "greater than" or "increased", "less than" or "decreased", or "equal to" said reference value for said gene. In the context of the present invention, it is considered that an expression level of the gene of interest in the sample from the subject is "greater than" or "increased with respect to" the reference value for said gene when the expression level of said gene in the sample from the subject increases, for example, 5%, 10%, 25%, 50%, 100% or even more when compared with the reference value for said gene, or when it increases, for example, at least 1.1-fold, 1.5-fold, 2-fold, 5-fold, 10-fold, 20-fold, 30-fold, 40-fold, 50-fold, 60-fold, 70-fold, 80-fold, 90-fold, 100-fold or even more when compared with the reference value for said gene. In the context of the present invention, it is also considered that an expression level of the gene of interest in the sample from the subject is "less than" or "decreased with respect to" the reference value for said gene when the expression level of said gene in the sample from the subject decreases, for example, 5%, 10%, 25%, 50%, 75%, or even 100% when compared with the reference value for said gene.

In the context of the present invention, it is also considered that an expression level of the gene of interest in the sample from the subject is "equal to" the reference value for said gene when the expression level of said gene is substantially unchanged with respect to the reference value; for example, it is considered that the expression level of a gene in the sample from the subject under study is "equal to" the reference value when the levels differ by not more than 0.1%, not more than 0.2%, not more than 0.3%, not more than 0.4%, not more than 0.5%, not more than 0.6%, not more than 0.7%, not more than 0.8%, not more than 0.9%, not more than 1%, not more than 2%, not more than 3%, not more than 4%, not more than 5%, or not more than the percentage value which is the same as the error associated with the experimental method used in the determination.

Once the comparison is made between the expression level of the IGF2 gene in the sample from the subject and the reference value for said gene, the first method of the invention allows diagnosing if a subject suffers bladder cancer based on if the expression level of the IGF2 gene in the sample from the subject under study is greater than said reference value.

The results obtained in Example 3 clearly show that using the expression level of the IGF2 gene allows diagnosing bladder cancer with a 76.85% sensitivity and a 91.26% specificity (AUC=0.907) in the multicentric validation cohort (Table 6).

Additionally, the authors of the present invention have observed that the IGF2 gene in combination with a second gene for diagnosing bladder cancer can be used for bladder cancer diagnosis. This finding allows establishing the bladder cancer diagnosis in a subject by means of a non-invasive method based on comparing the expression level of said IGF2 gene and of said second gene for diagnosing bladder cancer in the sample from the subject under study with its reference value.

Therefore, in another aspect, the invention relates to an in vitro method, hereinafter "second method of the invention", for diagnosing if a subject suffers bladder cancer which comprises:

a) determining the expression level of the IGF2 gene and the expression level of a second gene, wherein said second gene is selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes in a sample from said subject; and b) comparing the expression level of said genes in said sample with their reference values;

wherein an expression level of the IGF2 gene in the sample from the subject greater than the reference value for said gene; and wherein an altered expression level of said second gene in the sample from said subject when compared to the reference value for said gene, wherein said altered expression level is:

an increased expression level of the MAGEA3, ANXA10, CTSE, CRH, KRT20, POSTN, PPP1R14D, SLC1A6, TERT, ASAM, MCM10 or MMP12 genes, or a decreased expression level of the KLF9, AHNAK2, EBF1 or CFH genes, are indicative that said subject suffers bladder cancer.

In a first step, the second method of the invention comprises, or consists of, determining, in a sample from the subject under study, (i) the expression level of the IGF2 gene and (ii) the expression level of a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

The terms "diagnosis", "subject", "bladder cancer", "sample", "expression level" and "IGF2" have been previously defined in relation to the first method of the invention and are incorporated herein by reference.

As it is used herein, the term "MAGEA3" refers to insulin-like melanoma-associated antigen 3, also known as CT1.3, HIPS, HYPD, or MAGE3. The human MAGEA3 gene is located in chromosome X and has accession number NC_000023.10 in the GenBank database (version of 30 Oct. 2012).

As it is used herein, the term "ANXA10" refers to annexin A10, also known as ANX14. The human ANXA10 gene is located in chromosome 4 and has accession number NM_007193.4 in the GenBank database (version of 28 Jun. 2012).

As it is used herein, the term "AHNAK2" refers to neuroblast differentiation-associated protein AHKAK, also known as C14orf78 or KIAA2019. The human AHNAK2 gene is located in chromosome 14 and has accession number NM_001620.1 in the GenBank database (version of 5 Dec. 2012).

As it is used herein, the term "CTSE" refers to cathepsin E, also known as CATE4. The human CTSE gene is located in chromosome 1 and has accession number NM_001910.3 in the GenBank database (version of 12 Jan. 2013).

As it is used herein, the term "CRH" refers to corticotropin-releasing hormone, also known as CRF. The human CRH gene is located in chromosome 8 and has accession number NM_00756.2 in the GenBank database (version of 23 Dec. 2012).

As it is used herein, the term "KLF9" refers to Kruppel-like factor 9. The human KLF9 gene is located in chromosome 9 and has accession number NM_001206.2 in the GenBank database (version of 7 Jan. 2013).

As it is used herein, the term "KRT20" refers to keratin 20, also known as K20, CK20, KRT21, MGC35423. The human KRT20 gene is located in chromosome 17 and has accession number NC 000017.10 in the GenBank database (version of 30 Oct. 2012).

As it is used herein, the term "POSTN" refers to periostin, osteoblast specific factor. The human POSTN gene is located in chromosome 13 and has accession number NM_001135934.1 in the GenBank database (version of 28 Jan. 2013).

As it is used herein, the term "PPP1R14D" refers to protein phosphatase 1, regulatory (inhibitor) subunit 14D, also known as GBPI-1, FLJ20251, MGC119014, MGC119016, CPI17-like. The human PPP1R14D gene is located in chromosome 15 and has accession number NC 000015.9 in the GenBank database (version of 30 Oct. 2012).

As it is used herein, the term "SLC1A6" refers to solute carrier family 1 (high affinity aspartate/glutamate member 6), also known as EAA T 4, MGC33092 and MGC43671. The human SLC1A6 gene is located in chromosome 19 and has accession number NC 000019.9 in the GenBank database (version of 30 Oct. 2012).

As it is used herein, the term "TERT" refers to telomerase reverse transcriptase, also known as TP2, TRT, EST2, TCS1 and hEST2. The human TERT gene is located in chromosome 5 and has accession number NM_001193376.1 in the GenBank database (version of 28 Jan. 2013).

As it is used herein, the term "ASAM" refers to adipocyte-specific adhesion molecule, also known as ACAM, CLMP and FLJ22415. The human ASAM gene is located in chromosome 11 and has accession number NC 000011.9 in the GenBank database (version of 30 Oct. 2012).

As it is used herein, the term "MCM10" refers to minichromosome maintenance deficient 10 (*S. cerevisiae*), also known as CNA43, PR02249 and MGC126776. The human MCM10 gene is located in chromosome 10 and has accession number NM_182751.2 in the GenBank database (version of 24 Jan. 2013).

As it is used herein, the term "EBF1" refers to early B cell factor 1, also known as COE1, EBF and OLF1. The human EBF1 gene is located in chromosome 5 and has accession number NM_024007.3 in the GenBank database (version of 6 Jan. 2013).

As it is used herein, the term "CFH" refers to complement factor H, also known as HF, ARMS1 and FHL1. The human CFH gene is located in chromosome 1 and has accession number NM_001014975.2 in the GenBank database (version of 28 Jan. 2013).

As it is used herein the term "MMP12", refers to matrix (extracellular) metalloproteinase-2, also known as macrophage metalloestelase, macrophage estelase, HME, MME and MMP-12. The human MMP12 gene is located in chromosome 1 and has accession number NM_002426.4 in the GenBank database (version of 13 Jan. 2013).

The expression levels of the genes selected in this first step of the second method of the invention can be determined as mentioned in relation to the first method of the invention, i.e., by measuring the mRNA levels of the genes of interest (i.e., of the IGF2 gene and of a gene selected from the group consisting of the MAGEA3, ANXA10, AHNAK2, CTSE, CRH, KLF9, KRT20, POSTN, PPP1R14D, SLC1A6, TERT, ASAM MCM10, EBF1 CFH and MMP12 genes) or by measuring the amount of protein encoded by said genes of interest. The methods and techniques for determining the mRNA levels of the genes of interest or for measuring the amount of protein encoded by said genes of interest have been previously defined in relation to the first method of the invention and are incorporated herein by reference.

In a particular embodiment, the following is determined:
the expression level of the IGF2 gene, and
the expression level of a second gene, wherein said second gene is the MAGEA3 gene, or the ANXA10 gene, or the AHNAK2 gene, or the CTSE gene, or the CRH gene, or the KLF9 gene, or the KRT20 gene, or the POSTN gene, or the PPP1R14D gene, or the SLC1A6 gene, or the TERT gene, or the ASAM gene, or the MCM10 gene, or the EBF1 gene, or the CFH gene, or the MMP12 gene.

In a more particular embodiment, the following is determined:
the expression level of the IGF2 gene and
the expression level of a second gene wherein said selected second gene is selected form the group consisting of the CRH, KLF9, SLC1A6, MAGEA3, ANXA10 and KRT20 genes.

In a particular and preferred embodiment, the expression level of the IGF2 gene and the expression level of the MAGEA3 gene are determined.

In another particular embodiment, the expression level of the IGF2 gene and the expression level of the CRH gene are determined.

In another particular embodiment, the expression level of the IGF2 gene and the expression level of the KLF9 gene are determined.

In another particular embodiment, the expression level of the IGF2 gene and the expression level of the SLC1A6 gene are determined.

In another particular embodiment, the expression level of the IGF2 gene and the expression level of the ANXA10 gene are determined.

In another particular embodiment, the expression level of the IGF2 gene and the expression level of the AHNAK2 gene are determined.

In another particular embodiment, the expression level of the IGF2 gene and the expression level of the CTSE gene are determined.

In another particular embodiment, the expression level of the IGF2 gene and the expression level of the KRT20 gene are determined.

In another particular embodiment, the expression level of the IGF2 gene and the expression level of the POSTN gene are determined.

In another particular embodiment, the expression level of the IGF2 gene and the expression level of the PPP1R14D gene are determined.

In another particular embodiment, the expression level of the IGF2 gene and the expression level of the TERT gene are determined.

In another particular embodiment, the expression level of the IGF2 gene and the expression level of the ASAM gene are determined.

In another particular embodiment, the expression level of the IGF2 gene and the expression level of the MCM10 gene are determined.

In another particular embodiment, the expression level of the IGF2 gene and the expression level of the EBF1 gene are determined.

In another particular embodiment, the expression level of the IGF2 gene and the expression level of the CFH gene are determined.

In another particular embodiment, the expression level of the IGF2 gene and the expression level of the MMP12 gene are determined.

In the second step, the second method of the invention comprises, or consists of, comparing the expression levels obtained in the sample from the subject under study for the IGF2 gene and for a second gene selected from the group consisting of the MAGEA3, ANXA10, AHNAK2, CTSE, CRH, KLF9, KRT20, MAGEA3, POSTN, PPP1R14D, SLC1A6, TERT, ASAM, MCM10, EBF1, CFH and MMP12 genes with the reference values of said genes. The term "reference value" for establishing the reference level of a specific gene and the manner of obtaining it have been defined previously in relation to the first method of the invention and is herein incorporated by reference, as well as the terms "greater than", "less than" or "equal to" applied to the comparison between the expression levels of the genes of interest in the sample from the subject under study with their reference values.

Once the comparison has been made between the expression levels in the sample from the subject of the IGF2 gene and of a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes and the reference values for said genes, the second method of the invention allows diagnosing whether a subject suffers bladder cancer if:

the expression level of the IGF2 gene in the sample from said subject is greater than the reference value for said gene; and if the expression level of said second gene is altered when compared to the reference value for said gene wherein said altered expression level is:

an increased expression level of the MAGEA3, ANXA10, CTSE, CRH, KRT20, POSTN, PPP1R14D, SLC1A6, TERT, ASAM, MCM10 or MMP12 genes, or a decreased expression level of the KLF9, AHNAK2, EBF1 or CFH genes, The term "increased" applied to the expression level as used herein refers to an expression level above the reference value of at least 1.1-fold, 1.5-fold, 5-fold, 10-fold, 20-fold, 30-fold, 40-fold, 50-fold, 60-fold, 70-fold, 80-fold, 90-fold, 100-fold or even more compared with the reference value. On the other hand, a decrease in the expression level below the reference value of at least 5%, 10%, 25%, 50%, 75%, or even 100%, or alternatively expressed a decrease in the expression level below the reference value of at least 0.9-fold, 0.75-fold, 0.2-fold, 0.1-fold, 0.05-fold, 0.025-fold, 0.02-fold, 0.01-fold, 0.005-fold or even less compared with the reference value is considered as a "decreased" expression level.

The results obtained in Example 3 clearly show that using the expression level of the IGF2 gene in combination with the expression level of the MAGEA3 gene allows diagnosing bladder cancer with an 81.48% sensitivity and a 91.26% specificity, AUC=0.918 in the validation cohort (Table 6).

The results obtained in Example 3 clearly show that using the expression level of the IGF2 gene in combination with the expression level of the CRH gene allows diagnosing bladder cancer with a 75.46% sensitivity and a 90.94% specificity AUC=0.893) in the multicentric validation cohort (Table 6).

The results obtained in Example 3 clearly show that using the expression level of the IGF2 gene in combination with the expression level of the ANXA10 gene allows diagnosing bladder cancer with a 75.46% sensitivity and a 90.94% specificity (AUC=0.902) in the multicentric validation cohort (Table 6).

The results obtained in Example 3 clearly show that using the expression level of the IGF2 gene in combination with the expression level of the KRT20 gene allows diagnosing bladder cancer with a 76.39% sensitivity and a 92.23% specificity (AUC=0.907) in the multicentric validation cohort (Table 6).

Analyses performed by the inventors clearly show that using the expression level of the IGF2 gene in combination with the expression level of the KLF9 gene allows diagnosing bladder cancer with a 76.39% sensitivity and a 91.59% specificity (AUC=0.904).

Analyses performed by the inventors clearly show that using the expression level of the IGF2 gene in combination with the expression level of the SLC1A6 gene allows diagnosing bladder cancer with a 75.54% sensitivity and a 91.26% specificity (AUC=0.907).

Thus, in a particular embodiment, the second method of the invention for diagnosing if a subject suffers bladder cancer consists of:

a) determining the expression level of the IGF2 gene and the expression level of a second gene, wherein said second gene is selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes in a sample from said subject; and b) comparing the expression level of said genes in said sample with their reference values;

wherein an expression level of the IGF2, MAGEA3, ANXA10, CTSE, CRH, KRT20, POSTN, PPP1R14D, SLC1A6, TERT, ASAM, MCM10 and MMP12 genes in the sample from the subject greater than the reference values for each of said genes, and an expression level of the KLF9, AHNAK2, EBF1 and CFH genes in the sample from the subject less than the reference values for each of said genes, are indicative that said subject suffers bladder cancer.

In a particular and preferred embodiment, the expression level of the IGF2 gene and the expression level of the MAGEA3 gene are determined.

In another particular and preferred embodiment, the expression level of the IGF2 gene and the expression level of the CRH gene are determined. In another particular embodiment, the expression level of the IGF2 gene and the expression level of the KLF9 gene are determined. In another particular embodiment, the expression level of the IGF2 gene and the expression level of the SLC1A6 gene are determined. In another particular and preferred embodiment, the expression level of the IGF2 gene and the expression level of the ANXA10 gene are determined. In another particular embodiment, the expression level of the IGF2 gene and the expression level of the AHNAK2 gene are determined. In another particular embodiment, the expression level of the IGF2 gene and the expression level of the CTSE gene are determined. In another particular and preferred embodiment, the expression level of the IGF2 gene and the expression level of the KRT20 gene are determined. In another particular embodiment, the expression level of the IGF2 gene and the expression level of the POSTN gene are determined. In another particular embodiment, the expression level of the IGF2 gene and the expression level of the PPP1R14D gene are determined. In another particular embodiment, the expression level of the IGF2 gene and the expression level of the TERT gene are determined. In another particular embodiment, the expression level of the IGF2 gene and the expression level of the ASAM gene are determined. In another particular embodiment, the expression level of the IGF2 gene and the expression level of the MCM10 gene are determined. In another particular embodiment, the expression level of the IGF2 gene and the expression level of the EBF1 gene are determined. In another particular embodiment, the expression level of the IGF2 gene and the expression level of the CFH gene are determined. In another particular embodiment, the expression level of the IGF2 gene and the expression level of the MMP12 gene are determined.

Additionally, the authors of the present invention have observed that the IGF2 gene in combination with two or more genes for diagnosing bladder cancer can be used for bladder cancer diagnosis. This finding allows establishing the bladder cancer diagnosis in a subject by means of a non-invasive method based on comparing the expression level of said IGF2 gene in combination with two or more of said genes for diagnosing bladder cancer in the sample from the subject under study with its reference value.

Therefore, in another aspect, the invention relates to an in vitro method, hereinafter "third method of the invention", for diagnosing if a subject suffers bladder cancer which comprises:
  a) determining the expression level of each of the genes present in a combination of genes comprising the IGF2 gene, and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from said subject;
  b) comparing the level of said genes in said sample with their reference values;
wherein
  an expression level of the IGF2, MAGEA3, ANXA10, CTSE, CRH, KRT20, POSTN, PPP1R14D, SLC1A6, TERT, ASAM, MCM10 and MMP12 genes in the sample from the subject greater than the reference values for each of said genes, and
  an expression level of the KLF9, AHNAK2, EBF1 and CFH genes in the sample from the subject less than the reference values for each of said genes,
are indicative that said subject suffers bladder cancer.

In a first step, the third method of the invention comprises determining (i) the expression level of the IGF2 gene and (ii) the expression level of two or more genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from the subject under study.

The terms "diagnosis", "subject", "bladder cancer", "sample", "expression level", "IGF2", "MAGEA3", "ANXA10", "AHNAK2", "CTSE", "CRH", "KLF9", "KRT20", "POSTN", "PPP1R14D", "SLC1A6", "TERT", "ASAM", "MCM10", "EBF1", "CFH" and "MMP12" have been previously defined in relation to the second method of the invention and are incorporated herein by reference.

The expression levels of the genes selected in this first step of the third method of the invention can be determined as mentioned in relation to the first method of the invention, i.e., by measuring the mRNA levels of the genes of interest (i.e., of the IGF2 gene and of at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof) or by measuring the amount of protein encoded by said genes of interest. The methods and techniques for determining the mRNA levels of the genes of interest or for measuring the amount of protein encoded by said genes of interest have been previously defined in relation to the first method of the invention and are incorporated herein by reference.

In a particular embodiment, the third method of the invention comprises determining the expression level of each of the genes present in a combination of genes comprising the IGF2 gene, and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from said subject, with the proviso that said combination of genes is not any of the following combinations:
  ANXA10, AHNAK2, CTSE, CRH, KLF9, KRT20, MAGEA3, POSTN, PPP1R14D, SLC1A6, TERT, ASAM and MCM10;
  ANXA10, AHNAK2, CTSE, CRH, KLF9, KRT20, MAGEA3, POSTN, PPP1R14D, SLC1A6 and TERT;
  ANXA10, CRH, KRT20, MAGEA3, POSTN, SLC1A6 and TERT;
  ANXA10, CTSE, CRH, KRT20, MAGEA3, SLC1A6, TERT and MCM10; or
  ANXA10, CTSE, CRH, KRT20, MAGEA3, SLC1A6 and TERT.

Therefore, according to this particular embodiment of the third method of the invention, the invention provides an in vitro method for diagnosing if a subject suffers bladder cancer which comprises:
  a) determining the expression level of each of the genes present in a combination of genes comprising the IGF2 gene, and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from said subject, with the proviso that said combination of genes is not any of the following combinations:
    ANXA10, AHNAK2, CTSE, CRH, KLF9, KRT20, MAGEA3, POSTN, PPP1R14D, SLC1A6, TERT, ASAM and MCM10;
    ANXA10, AHNAK2, CTSE, CRH, KLF9, KRT20, MAGEA3, POSTN, PPP1R14D, SLC1A6 and TERT;

ANXA10, CRH, KRT20, MAGEA3, POSTN, SLC1A6 and TERT;

ANXA10, CTSE, CRH, KRT20, MAGEA3, SLC1A6, TERT and MCM10; or

ANXA10, CTSE, CRH, KRT20, MAGEA3, SLC1A6 and TERT; and b) comparing the level of said genes in said sample with their reference values;

wherein an expression level of the IGF2, MAGEA3, ANXA10, CTSE, CRH, KRT20, POSTN, PPP1R14D, SLC1A6, TERT, ASAM, MCM10 and MMP12 genes in the sample from the subject greater than the reference values for each of said genes, and an expression level of the KLF9, AHNAK2, EBF1 and CFH genes in the sample from the subject less than the reference values for each of said genes, are indicative that said subject suffers bladder cancer.

In a particular embodiment of the third method of the invention, it is determined the expression level of the IGF2 gene and the expression level of 2 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 3 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 4 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 5 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 6 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 7 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 7 genes is not the combination of ANXA10, CRH, KRT20, MAGEA3, POSTN, SLC1A6 and TERT or the combination of ANXA10, CTSE, CRH, KRT20, MAGEA3, SLC1A6 and TERT.

In a particular embodiment of the third method of the invention, it is determined the expression level of the IGF2 gene and the expression level of 8 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 8 genes is not the combination of ANXA10, CTSE, CRH, KRT20, MAGEA3, SLC1A6, TERT and MCM10.

In a particular embodiment of the third method of the invention, it is determined the expression level of the IGF2 gene and the expression level of 9 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 10 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 11 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 11 genes is not the combination of ANXA10, AHNAK2, CTSE, CRH, KLF9, KRT20, MAGEA3, POSTN, PPP1R14D, SLC1A6 and TERT.

In a particular embodiment of the third method of the invention, it is determined the expression level of the IGF2 gene and the expression level of 12 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 13 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 13 genes is not the combination of ANXA10, AHNAK2, CTSE, CRH, KLF9, KRT20, MAGEA3, POSTN, PPP1R14D, SLC1A6, TERT, ASAM and MCM10.

In a particular embodiment of the third method of the invention, it is determined the expression level of the IGF2 gene and the expression level of 14 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of 15 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment of the third method of the invention, it is determined the expression level of the IGF2 gene and the expression level of the 16 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the expression level of the IGF2, MAGEA3 and KLF9 genes is determined.

In another particular embodiment, the expression level of the IGF2, MAGEA3 and SLC1A6 genes is determined.

In another particular embodiment, the expression level of the IGF2, MAGEA3 and CRH genes is determined.

In another particular embodiment, the expression level of the IGF2, KLF9 and SLC1A6 genes is determined.

In another particular embodiment, the expression level of the IGF2, CRH and SLC1A6 genes is determined.

In another particular embodiment, the expression level of the IGF2, CRH and KLF9 genes is determined.

In another particular embodiment, the expression level of the IGF2, CRH and KRT20 genes is determined.

In another particular embodiment, the expression level of the IGF2, CRH and ANXA10 genes is determined.

In another particular embodiment, the expression level of the IGF2, ANXA10 and KRT20 genes is determined.

In another particular embodiment, the expression level of the IGF2, CRH, KLF9 and SLC1A6 genes is determined.

In another particular embodiment, the expression level of the IGF2, MAGEA3, KLF9 and CRH genes is determined.

In another particular embodiment, the expression level of the IGF2, MAGEA3, CTSE and MMP12 genes is determined.

In another particular embodiment, the expression level of the IGF2, MAGEA3, CRH, KLF9 and SLC1A6 genes is determined.

In another particular embodiment, the expression level of the IGF2, MAGEA3, KLF9, ANHAK2, BFE1 and MMP12 genes is determined.

In another particular embodiment, the expression level of the IGF2, MAGEA3, KLF9, PPP1R14D, SLC1A6 and ASAM genes is determined.

In another particular embodiment, the expression level of the IGF2, MAGEA3, KLF9, PPP1R14D, SLC1A6 and MCM10 genes is determined.

In another particular embodiment, the expression level of the IGF2, MAGEA3, CRH, KLF9, SLC1A6, EBF1 and CFH genes is determined.

In another particular embodiment, the expression level of the IGF2, MAGEA3, CRH, KLF9, PPP1R14D, SLC1A6 and EBF1 genes is determined.

In another particular embodiment, the expression level of the IGF2, MAGEA3, CRH, KLF9, PPP1R14D, SLC1A6, EBF1 and CFH genes is determined.

In another particular embodiment, the expression level of the IGF2, MAGEA3, CRH, PPPR14D, SLC1A6, EBF1, CFH and MMP12 genes is determined.

In another particular embodiment, the expression level of the IGF2, MAGEA3, CRH, KLF9, PPP1R14D, SLC1A6, EBF1, CFH and MMP12 genes is determined.

In another particular embodiment, the expression level of the IGF2, MAGEA3, POSTN, TERT, ASAM, MCM10, EBF1, CFH and MMP12 genes is determined.

In another particular embodiment, the expression level of the IGF2, MAGEA3, CRH, KLF9, SLC1A6, POSTN, EBF1, CFH, MCM10 and MMP12 genes is determined.

Optionally, if desired, in a particular embodiment, the third method of the invention includes furthermore determining the expression level of one or more of the genes selected from the group consisting of the FOXM1, KIF20A, MELK and CDK1 genes and any combination thereof.

As it is used herein, the term "FOXM1" refers to the FOXM1 (Forkhead box protein M1) proto-oncogene, also known as FKHL16, FOXM1B, HFH-11, HFN-3, INS-1, MPHOSPH2 and MPP-2. The human FOXM1 gene is located in chromosome 12 and has accession number NM_001243088.1 in the GenBank database (version of 28 Jan. 2013).

As it is used herein, the term "KIF20A" refers to the kinesin-like protein, also known as MKLP2 and RAB6KIFL. The human KIF20 gene is located in chromosome 5 and has accession number NM_005733.2 in the GenBank database (version of 27 Jan. 2013).

As it is used herein, the term "MELK" refers to the maternal embryonic leucine zipper kinase protein, also known as HPK38. The human MELK gene is located in chromosome 9 and has accession number NM_001256685.1 in the GenBank database (version of 13 Jan. 2013).

As it is used herein, the term "CDK1" refers to cyclin-dependent kinase 1, also known as CDC2, CDC28A and P34CDC2. The CDK1 gene is located in chromosome 10 and has accession number NM_001130829.1 in the GenBank database (version of 1 Nov. 2009).

In a particular embodiment, the expression level of the IGF2, MAGEA3, CRH, KLF9, SLC1A6, POSTN, EBF1, CFH, MCM10, MMP12, TERT, FOXM1, KIF20A, MELK and CDK1 genes is determined.

Analyses performed by the inventors clearly show that using the expression level of the IGF2, MAGEA3 and CRH genes allows the diagnosis of bladder cancer with a 77.78% sensitivity and a 93.2% specificity (AUC=0.904).

Analyses performed by the inventors clearly show that using the expression level of the IGF2, KLF9 and SLC1A6 genes allows the diagnosis of bladder cancer with a 77.31% sensitivity and an 89.32% specificity (AUC=0.903).

Analyses performed by the inventors clearly show that using the expression level of the IGF2, CRH and SLC1A6 genes allows the diagnosis of bladder cancer with a 75% sensitivity and a 91.26% specificity (AUC=0.897).

Analyses performed by the inventors clearly show that using the expression level of the IGF2, CRH and KLF9 genes allows the diagnosis of bladder cancer with a 77.78% sensitivity and a 91.59% specificity (AUC=0.897).

The results obtained in Example 3 clearly show that using the expression level of the IGF2, CRH and KRT20 genes allows the diagnosis of bladder cancer with a 75.93% sensitivity and a 90.94% specificity (AUC=0.895) in the multicentric validation cohort (Table 6).

Analyses performed by the inventors clearly show that using the expression level of the IGF2, CRH, KLF9 and SLC1A6 genes allows the diagnosis of bladder cancer with a 76.17% sensitivity and a 91.59% specificity (AUC=0.902).

The results obtained in Example 3 clearly show that using the expression level of the IGF2, MAGEA3, CRH, KLF9 and SLC1A6 genes allows the diagnosis of bladder cancer with a 79.17% sensitivity and a 91.59% specificity (AUC=0.903) in the multicentric validation cohort (Table 6).

The results obtained in Example 3 clearly show that using the expression level of the IGF2, MAGEA3, CRH, KLF9, SLC1A6, POSTN, EBF1, CFH, MCM10 and MMP12 genes allows the diagnosis of bladder cancer with a 79.63% sensitivity and a 93.53% specificity (AUC=0.908) in the multicentric validation cohort (Table 6).

Analyses performed by the inventors clearly show that using the expression level of the IGF2, MAGEA3, CRH, KLF9, SLC1A6, POSTN, EBF1, CFH, MCM10, MMP12, TERT, FOXM1, KIF20A, MELK and CDK1 genes allows the diagnosis of bladder cancer with a 79.63% sensitivity and an 89.97% specificity (AUC=0.909).

In another aspect, the invention relates to a method for diagnosing if a subject suffers bladder cancer, hereinafter "fourth method of the invention", which comprises:
- a) determining the expression level of the IGF2 gene in a sample from said subject;
- b) comparing the expression level of said IGF2 gene in said sample with its reference value;
    - wherein an expression level of the IGF2 gene in the sample from the subject greater than said reference value for said gene is indicative that said subject suffers bladder cancer; and
- a) subjecting the subject to an endoscopic procedure if the subject suffers bladder cancer according to the expression level of the said genes.

In another aspect, the invention relates to a method for diagnosing a subject who suffers bladder cancer, hereinafter referred to as the "fifth method of the invention", which comprises:
- a) determining the expression level of the IGF2 gene and the expression level of a second gene, wherein said second gene is selected from the group consisting of the MAGEA3, ANXA10, AHNAK2, CTSE, CRH, KLF9, KRT20, POSTN, PPP1R14D, SLC1A6, TERT, ASAM MCM10, EBF1, CFH and MMP12 genes in a urine sample from said subject;
- b) comparing the expression level of said genes in said sample with their reference values;
    - wherein an expression level of the IGF2 gene in the sample from the subject greater than the reference value for said gene; and
    - wherein an altered expression level of said second gene in the sample from said subject when compared to the reference value for said gene, wherein said altered expression level is:
        - an increased expression level of the MAGEA3, ANXA10, CTSE, CRH, KRT20, POSTN, PPP1R14D, SLC1A6, TERT, ASAM, MCM10 or MMP12 genes, or
        - a decreased expression level of the KLF9, AHNAK2, EBF1 or CFH genes,
    - are indicative that said subject suffers bladder cancer; and
- c) subjecting the subject to an endoscopic procedure if the subject suffers bladder cancer according to the expression level of the said genes.

In another aspect, the invention relates to a method for diagnosing a subject who suffers bladder cancer, hereinafter referred to as the "sixth method of the invention", which comprises:
- a) determining the expression level of each of the genes present in a combination of genes comprising the IGF2 gene, and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from said subject;
- b) comparing the level of said genes in said sample with their reference values;
    - wherein
        - an expression level of the IGF2, MAGEA3, ANXA10, CTSE, CRH, KRT20, POSTN, PPP1R14D, SLC1A6, TERT, ASAM, MCM10 and MMP12 genes in the sample from the subject greater than the reference values for each of said genes, and
        - an expression level of the KLF9, AHNAK2, EBF1 and CFH genes in the sample from the subject less than the reference values for each of said genes,
    - are indicative that said subject suffers bladder cancer; and
- c) subjecting the subject to an endoscopic procedure if the subject suffers bladder cancer according to the expression level of the said genes.

The particulars of steps a) and b) of the fourth, fifth and sixth methods of the invention have been previously mentioned in connection with the first, second and third methods of the invention, respectively, and are incorporated herein by reference. Said steps are performed in vitro.

Step c) of the fourth, fifth and sixth methods of the invention, in other words, comprises prescribing or performing an endoscopic procedure if the diagnosis is positive for bladder cancer. Thus, briefly, if the subject is diagnosed as suffering bladder cancer, then the subject is subjected to an endoscopic procedure, e.g., cystoscopy. Cystoscopy is endoscopy of the urinary bladder via the urethra. It is carried out with a cystoscope, i.e., a device that has lenses which let the physician focus on the bladder mucosa. Some cystoscopes use optical fibres (flexible glass fibres) that carry an image from the tip of the instrument to a viewing piece at the other end. Many cystoscopes have extra tubes to guide other instruments for surgical procedures to treat urinary problems. There are two main types of cystoscopy, namely flexible and rigid, differing in the flexibility of the cystoscope. Flexible cystoscopy is usually carried out with local anaesthesia. Rigid cystoscopy is generally carried out under general anaesthesia due to the pain caused by the probe.

If, according to any of the methods for diagnosing bladder cancer according to the present invention [i.e., the first, second or third method of the invention], the subject is diagnosed as not suffering bladder cancer, the subject would not be subjected to an endoscopic procedure.

In another aspect, the invention relates to a method for treating a subject who suffers bladder cancer, hereinafter referred to as the "seventh method of the invention", which comprises:
- a) determining the expression level of the IGF2 gene in a sample from said subject;
- b) comparing the expression level of said IGF2 gene in said sample with its reference value;
    - wherein an expression level of the IGF2 gene in the sample from the subject greater than said reference value for said gene is indicative that said subject suffers bladder cancer; and
- c) administering a transurethral resection (TUR) to the subject if the subject is diagnosed as suffering bladder cancer and said subject will benefit from the administration of said therapy.

In another aspect, the invention relates to a method for treating a subject who suffers bladder cancer, hereinafter referred to as the "eighth method of the invention", which comprises:
- a) determining the expression level of the IGF2 gene and the expression level of a second gene, wherein said second gene is selected from the group consisting of the MAGEA3, ANXA10, AHNAK2, CTSE, CRH, KLF9, KRT20, POSTN, PPP1R14D, SLC1A6, TERT, ASAM MCM10, EBF1, CFH and MMP12 genes in a urine sample from said subject;

b) comparing the expression level of said genes in said sample with their reference values;
  wherein an expression level of the IGF2 gene in the sample from the subject greater than the reference value for said gene; and
  wherein an altered expression level of said second gene in the sample from said subject when compared to the reference value for said gene, wherein said altered expression level is:
    an increased expression level of the MAGEA3, ANXA10, CTSE, CRH, KRT20, POSTN, PPP1R14D, SLC1A6, TERT, ASAM, MCM10 or MMP12 genes, or
    a decreased expression level of the KLF9, AHNAK2, EBF1 or CFH genes,
  are indicative that said subject suffers bladder cancer; and
c) administering a transurethral resection (TUR) to the subject if the subject is diagnosed as suffering bladder cancer and said subject will benefit from the administration of said therapy.

In another aspect, the invention relates to a method for treating a subject who suffers bladder cancer, hereinafter referred to as the "ninth method of the invention", which comprises:
a) determining the expression level of each of the genes present in a combination of genes comprising the IGF2 gene, and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof in a sample from said subject;
b) comparing the level of said genes in said sample with their reference values;
  wherein
    an expression level of the IGF2, MAGEA3, ANXA10, CTSE, CRH, KRT20, POSTN, PPP1R14D, SLC1A6, TERT, ASAM, MCM10 and MMP12 genes in the sample from the subject greater than the reference values for each of said genes, and
    an expression level of the KLF9, AHNAK2, EBF1 and CFH genes in the sample from the subject less than the reference values for each of said genes,
  are indicative that said subject suffers bladder cancer; and
c) administering a transurethral resection (TUR) to the subject if the subject is diagnosed as suffering bladder cancer and said subject will benefit from the administration of said therapy.

The particulars of steps a) and b) of the seventh, eighth and ninth methods of the invention have been previously mentioned in connection with the first, second and third methods of the invention, respectively, and are incorporated herein by reference. Said steps are performed in vitro.

According to step c) of the seventh, eighth and ninth methods of the invention, the subject is diagnosed as suffering bladder cancer by any of the first, second or third methods of the invention, then a therapy is administered to said subject who will benefit from the administration of said therapy.

As it is well-known, the treatment of bladder cancer depends on how deep the tumor invades into the bladder wall. All patients go as a first step for a TUR. Non muscle invasive bladder cancer (NMIBC) (those not entering the muscle layer) can be removed using an electrocautery device attached to a cystoscope, which in that case is called a resectoscope. The procedure is called TUR and serves primarily for pathological staging. In case of non-muscle invasive bladder cancer the TUR is in itself the treatment, but in case of muscle invasive bladder cancer (MIBC), the procedure is insufficient for final treatment.

Immunotherapy by intravesicular delivery of *Bacillus* Calmette-Guérin (BCG) is also used to treat and prevent the recurrence of NMIBC. BCG is a vaccine against tuberculosis that is prepared from attenuated (weakened) live bovine tuberculosis *bacillus, Mycobacterium bovis*, that has lost its virulence in humans. BCG immunotherapy is effective in up to ⅔ of the cases at this stage, and in randomized trials has been shown to be superior to standard chemotherapy.

Instillations of intravesical chemotherapy, such as mytomicine and other are valid options to treat and prevent recurrences. Device assisted chemotherapy is one such group of novel technologies used to treat NMIBC. These technologies use different mechanisms to facilitate the absorption and action of a chemotherapy drug instilled directly into the bladder. Another technology uses an electrical current to enhance drug absorption. Another technology, thermotherapy, uses radio-frequency energy to directly heat the bladder wall, which together with chemotherapy shows a synergistic effect, enhancing each other's capacity to kill tumor cells.

Patients whose tumors recurred after treatment with BCG are more difficult to treat. Many physicians recommend cystectomy for these patients. This recommendation is in accordance with the official guidelines of the European Association of Urologists (EAU) and the American Urological Association (AUA). However, patients may prefer to try conservative treatment options before opting to this last radical option treatment. Untreated, superficial tumors may progress and infiltrate the muscular wall of the bladder. Tumors that infiltrate the muscle layer of the bladder require more radical surgery where usually all the bladder is removed (a procedure called cystectomy) and the urinary stream is diverted into an isolated bowel loop (called an ileal conduit or Urostomy). In some cases, skilled surgeons can create a substitute bladder (a neobladder) from a segment of intestinal tissue, but this largely depends upon patient preference, age of patient, renal function, and the site of the disease.

A combination of radiation and chemotherapy can also be used to treat invasive disease. It has not yet been determined how the effectiveness of this form of treatment compares to that of radical ablative surgery.

For muscle invasive urothelial urinary bladder cancer there are a number of treatment options. Gold standard is radical cystectomy as mentioned. In males this usually includes also the removal of the prostate and in females; ovaries, uterus and parts of the vagina. In order to address the problem of micrometastatic disease which in itself has implications on longtime survival, new treatment options are needed. Micrometastatic dissemination is often not treatable with only major surgery and the concept of neoadjuvant chemotherapy has evolved. In a number of meta-analyses of randomised prospective trials worldwide, the results have shown survival benefits between 5-8% with this therapy, in a follow up time of 5 years. Thus patients first receive chemotherapy in 3 or 4 cycles, and first after that proceed to major surgery.

If, according to any of the methods for diagnosing bladder cancer according to the present invention [i.e., the first, second or third method of the invention], the subject is diagnosed as not suffering bladder cancer, the subject would not be subjected to any treatment.

In view of the results provided by this invention, the physician could optimize the diagnosis of bladder cancer to apply to the subject by choosing the suitable approach (e.g., cystoscopy). Therefore, the methods and means provided by the present invention can help physicians to select the most suitable diagnosis option for a subject who may suffer bladder cancer. Further, the discomfort caused to the subject associated with the application of invasive diagnosis methods that are not necessary as well as the unnecessary cost involved in that case, can be prevented.

Uses Of The Invention

In another aspect, the invention relates to the use of the IGF2 gene as a marker in bladder cancer diagnosis or for bladder cancer monitoring.

In another aspect, the invention relates to the use of a combination of genes comprising, or consisting of, the IGF2 gene and a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes as a marker in bladder cancer diagnosis or for bladder cancer monitoring.

In a particular embodiment, said second gene is MAGEA3.

In another particular embodiment, said second gene is CRH.

In another particular embodiment, said second gene is KLF9.

In another particular embodiment said second gene is SLC1A6.

In another particular embodiment said second gene is ANXA10.

In another particular embodiment said second gene is AHNAK2.

In another particular embodiment said second gene is CTSE.

In another particular embodiment said second gene is KRT20.

In another particular embodiment said second gene is POSTN.

In another particular embodiment said second gene is PPP1R14D.

In another particular embodiment said second gene is TERT.

In another particular embodiment said second gene is ASAM.

In another particular embodiment said second gene is MCM10.

In another particular embodiment said second gene is EBF1.

In another particular embodiment said second gene is CFH.

In another particular embodiment said second gene is MMP12.

In another aspect, the invention relates to the use of a combination of genes comprising the IGF2 gene and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof, with the proviso that said combination is not any of the following combinations:

ANXA10, AHNAK2, CTSE, CRH, KLF9, KRT20, MAGEA3, POSTN, PPP1R14D, SLC1A6, TERT, ASAM and MCM10;

ANXA10, AHNAK2, CTSE, CRH, KLF9, KRT20, MAGEA3, POSTN, PPP1R14D, SLC1A6 and TERT;

ANXA10, CRH, KRT20, MAGEA3, POSTN, SLC1A6 and TERT;

ANXA10, CTSE, CRH, KRT20, MAGEA3, SLC1A6, TERT and MCM10; or

ANXA10, CTSE, CRH, KRT20, MAGEA3, SLC1A6 and TERT;

as a marker in bladder cancer diagnosis or for bladder cancer monitoring.

In a particular embodiment, the combination of genes comprises the IGF2 gene and 2 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 3 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 4 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 5 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 6 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 7 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 7 genes is not the combination of ANXA10, CRH, KRT20, MAGEA3, POSTN, SLC1A6 and TERT or the combination of ANXA10, CTSE, CRH, KRT20, MAGEA3, SLC1A6 and TERT.

In a particular embodiment, the combination of genes comprises the IGF2 gene and 8 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 8 genes is not the combination of ANXA10, CTSE, CRH, KRT20, MAGEA3, SLC1A6, TERT and MCM10.

In a particular embodiment, the combination of genes comprises the IGF2 gene and 9 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 10 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 11 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 11 genes is not the combination of ANXA10, AHNAK2, CTSE, CRH, KLF9, KRT20, MAGEA3, POSTN, PPP1R14D, SLC1A6 and TERT.

In a particular embodiment, the combination of genes comprises the IGF2 gene and 12 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 13 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said combination of 13 genes is not the combination of ANXA10, AHNAK2, CTSE, CRH, KLF9, KRT20, MAGEA3, POSTN, PPP1R14D, SLC1A6, TERT, ASAM and MCM10.

In a particular embodiment, the combination of genes comprises the IGF2 gene and 14 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 15 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the combination of genes comprises the IGF2 gene and 16 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, said combination of genes comprises, or consists of, the IGF2, MAGEA3 and KLF9 genes.

In another particular embodiment, said combination of genes comprises, or consists of, the IGF2, MAGEA3 and SLC1A6 genes.

In another particular embodiment, said combination of genes comprises, or consists of, the IGF2, MAGEA3 and CRH genes.

In another particular embodiment, said combination of genes comprises, or consists of, the IGF2, KLF9 and SLC1A6 genes.

In another particular embodiment, said combination of genes comprises, or consists of, the IGF2, CRH and SLC1A6 genes.

In another particular embodiment, said combination of genes comprises, or consists of, the IGF2, CRH and KLF9 genes.

In another particular embodiment, said combination of genes comprises, or consists of, the IGF2, CRH and KRT20 genes.

In another particular embodiment, said combination of genes comprises, or consists of, the IGF2, CRH and ANXA10 genes.

In another particular embodiment, said combination of genes comprises, or consists of, the IGF2, ANXA10 and KRT20 genes.

In another particular embodiment, said combination of genes comprises, or consists of, the IGF2, CRH, KLF9 and SLC1A6 genes.

In another particular embodiment, said combination of genes comprises, or consists of, the IGF2, MAGEA3, KLF9 and CRH genes.

In another particular embodiment, said combination of genes comprises, or consists of, the IGF2, MAGEA3, CTSE and MMP12 genes.

In another particular embodiment, said combination of genes comprises, or consists of, the IGF2, MAGEA3, CRH, KLF9 and SLC1A6 genes.

In another particular embodiment, said combination of genes comprises, or consists of, the IGF2, MAGEA3, KLF9, ANHAK2, BFE1 and MMP12 genes.

In another particular embodiment, said combination of genes comprises, or consists of, the IGF2, MAGEA3, KLF9, PPP1R14D, SLC1A6 and ASAM genes.

In another particular embodiment, said combination of genes comprises, or consists of, the IGF2, MAGEA3, KLF9, PPP1R14D, SLC1A6 and MCM10 genes.

In another particular embodiment, said combination of genes comprises, or consists of, the IGF2, MAGEA3, CRH, KLF9, SLC1A6, EBF1 and CFH genes.

In another particular embodiment, said combination of genes comprises, or consists of, the IGF2, MAGEA3, CRH, KLF9, PPP1R14D, SLC1A6 and EBF1 genes.

In another particular embodiment, said combination of genes comprises, or consists of, the IGF2, MAGEA3, CRH, KLF9, PPP1R14D, SLC1A6, EBF1 and CFH genes.

In another particular embodiment, said combination of genes comprises, or consists of, the IGF2, MAGEA3, CRH, PPP1R14D, SLC1A6, EBF1, CFH and MMP12 genes.

In another particular embodiment, said combination of genes comprises, or consists of, the IGF2, MAGEA3, CRH, KLF9, PPP1R14D, SLC1A6, EBF1, CFH and MMP12 genes.

In another particular embodiment, said combination of genes comprises, or consists of, the IGF2, MAGEA3, POSTN, TERT, ASAM, MCM10, EBF1, CFH and MMP12 genes.

In another particular embodiment, said combination of genes comprises, or consists of, the IGF2, MAGEA3, CRH, KLF9, SLC1A6, POSTN, MCM10, EBF1, CFH and MMP12 genes.

In another particular embodiment, said combination of genes comprises, or consists of, the IGF2, MAGEA3, CRH, KLF9, SLC1A6, POSTN, EBF1, CFH, MCM10, MMP12, TERT, FOXM1, KIF20A, MELK and CDK1 genes.

As the skilled person in the art may understand, the teachings of the invention can also be applied to monitor or follow up the periodic or repetitive diagnosis along the time in patients who have previously suffered bladder cancer and who have been treated but who should still be under vigilance due to the high risk of recurrence of this kind of cancer. Typically, patients are monitored at different time intervals ranging usually between 3 months and 1 year from the last treatment.

Therefore, in another aspect, the invention relates to the use of any of the genes or combinations thereof provided by the instant invention for bladder cancer monitoring. The particulars of said genes and gene combinations provided by the invention have been previously mentioned and are included herein by reference.

Kits Of The Invention

In another aspect, the invention relates to a kit, hereinafter "first kit of the invention", comprising a reagent for detecting and/or quantifying the expression level of the IGF2 gene.

In a particular embodiment, said reagent is a reagent for detecting and/or quantifying an mRNA of the IGF2 gene. In another particular embodiment, said reagent is a reagent for detecting and/or quantifying the protein encoded by the IGF2 gene.

In a particular embodiment, said reagent for detecting and/or quantifying an mRNA of the IGF2 gene comprises a probe which hybridizes with a cDNA to said mRNA of IGF2 or a pair of oligonucleotide primers which hybridizes with said mRNA of IGF2 or with said cDNA to said mRNA of IGF2.

In another particular embodiment, said reagent for detecting and/or quantifying the protein encoded by the IGF2 gene is an antibody that recognizes IGF2.

In another aspect, the invention relates to a kit, hereinafter "second kit of the invention", comprising a reagent for detecting and/or quantifying the expression level of a combination of genes comprising, or consisting of, the IGF2 gene and a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, said kit comprises a reagent for detecting and/or quantifying an mRNA of the IGF2 gene and a reagent for detecting and/or quantifying an mRNA of a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes. In a particular embodiment, said reagent for detecting and/or quantifying an mRNA of the IGF2 gene comprises a probe which hybridizes with a cDNA to said mRNA of IGF2 or a pair of oligonucleotide primers which hybridizes with said mRNA of IGF2 or with said cDNA to said mRNA of IGF2. In a particular embodiment, said reagent for detecting and/or quantifying an mRNA of a second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes comprise a probe which hybridizes with a cDNA to the mRNA of said second gene, or a pair of oligonucleotide primers which hybridizes with said mRNA of said second gene or with said cDNA to said mRNA of said second gene. In a specific particular embodiment, said kit comprises a reagent for detecting and/or quantifying an mRNA of the IGF2 gene and a reagent for detecting and/or quantifying an mRNA of a second gene selected from the group consisting of the MAGEA3 gene, wherein said reagent for detecting and/or quantifying an mRNA of the IGF2 gene comprises a probe which hybridizes with a cDNA to said mRNA of IGF2 or a pair of oligonucleotide primers which hybridizes with said mRNA of IGF2 or with said cDNA to said mRNA of IGF2, and wherein said reagent for detecting and/or quantifying an mRNA of the MAGEA3 gene comprises a probe which hybridizes with a cDNA to said mRNA of MAGEA3 or a pair of oligonucleotide primers which hybridizes with said mRNA of MAGEA3 or with said cDNA to said mRNA of MAGEA3. In other specific embodiments the second gene to be detected and/or quantified is CRH, KRT20, SLC1A6, ANXA10 or KLF9.

In another particular embodiment, said reagent for detecting and/or quantifying the protein encoded by the IGF2 gene is an antibody that recognizes IGF2. In another particular embodiment, said reagent for detecting and/or quantifying the protein encoded by said second gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes is an antibody that recognizes the protein encoded by said second gene.

In a particular embodiment, said reagent for detecting and/or quantifying the protein encoded by the second marker gene is an antibody that recognizes MAGEA3.

In a particular embodiment, said reagent for detecting and/or quantifying the protein encoded by the second marker gene is an antibody that recognizes CRH.

In a particular embodiment, said reagent for detecting and/or quantifying the protein encoded by the second marker gene is an antibody that recognizes KLF9.

In a particular embodiment, said reagent for detecting and/or quantifying the protein encoded by the second marker gene is an antibody that recognizes SLC1A6.

In a particular embodiment, said reagent for detecting and/or quantifying the protein encoded by the second marker gene is an antibody that recognizes ANXA10.

In a particular embodiment, said reagent for detecting and/or quantifying the protein encoded by the second marker gene is an antibody that recognizes AHNAK2.

In a particular embodiment, said reagent for detecting and/or quantifying the protein encoded by the second marker gene is an antibody that recognizes CTSE.

In a particular embodiment, said reagent for detecting and/or quantifying the protein encoded by the second marker gene is an antibody that recognizes KRT20.

In a particular embodiment, said reagent for detecting and/or quantifying the protein encoded by the second marker gene is an antibody that recognizes POSTN.

In a particular embodiment, said reagent for detecting and/or quantifying the protein encoded by the second marker gene is an antibody that recognizes PPP1R14D.

In a particular embodiment, said reagent for detecting and/or quantifying the protein encoded by the second marker gene is an antibody that recognizes TERT.

In a particular embodiment, said reagent for detecting and/or quantifying the protein encoded by the second marker gene is an antibody that recognizes ASAM.

In a particular embodiment, said reagent for detecting and/or quantifying the protein encoded by the second marker gene is an antibody that recognizes MCM10.

In a particular embodiment, said reagent for detecting and/or quantifying the protein encoded by the second marker gene is an antibody that recognizes EBF1.

In a particular embodiment, said reagent for detecting and/or quantifying the protein encoded by the second marker gene is an antibody that recognizes CFH.

In a particular embodiment, said reagent for detecting and/or quantifying the protein encoded by the second marker gene is an antibody that recognizes MMP12.

In another aspect, the invention relates to a kit, hereinafter "third kit of the invention", comprising a reagent for detecting and/or quantifying the expression level of a combination of genes comprising the IGF2 gene and at least two genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and any combination thereof, with the proviso that said combination is not any of the following combinations:

ANXA10, AHNAK2, CTSE, CRH, KLF9, KRT20, MAGEA3, POSTN, PPP1R14D, SLC1A6, TERT, ASAM and MCM10;

ANXA10, AHNAK2, CTSE, CRH, KLF9, KRT20, MAGEA3, POSTN, PPP1R14D, SLC1A6 and TERT;

ANXA10, CRH, KRT20, MAGEA3, POSTN, SLC1A6 and TERT;

ANXA10, CTSE, CRH, KRT20, MAGEA3, SLC1A6, TERT and MCM10; or

ANXA10, CTSE, CRH, KRT20, MAGEA3, SLC1A6 and TERT.

In a particular embodiment, said third kit of the invention comprises a reagent for detecting and/or quantifying an mRNA of the IGF2 gene and two or more reagents for detecting and/or quantifying an mRNA of a gene selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and combinations thereof. In a particular embodiment, said reagent for detecting and/or quantifying an mRNA of the IGF2 gene comprises a probe which hybridizes with a cDNA to said mRNA of IGF2 or a pair of oligonucleotide primers which hybridizes with said mRNA of IGF2 or with said cDNA to said mRNA of IGF2. In another particular embodiment, said reagents for detecting and/or quantifying mRNA of the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and combinations thereof comprise probes which hybridize with cDNA to the mRNA of said genes, or pairs of oligonucleotide primers which hybridize with said mRNAs of said genes or with said cDNAs to said mRNAs of said genes. In another particular embodiment, said reagents for detecting and/or quantifying the proteins encoded by the IGF2 gene and by the MAGEA3, ANXA10, AHNAK2, CTSE, CRH, KLF9, KRT20, POSTN, PPP1R14D, SLC1A6, TERT, ASAM, MCM10, EBF1, CFH, MMP12 genes and combinations thereof are antibodies that recognize proteins encoded by said genes.

In a particular embodiment, the third kit of the invention comprises one or more reagents for detecting and/or quantifying the expression level of the IGF2 gene and one or more reagents for detecting and/or quantifying the expression level of 2 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 3 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 4 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 5 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 6 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 7 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said kit does not consists of reagents for detecting and/or quantifying the expression level of the following gene combinations: IGF2, ANXA10, CRH, KRT20, MAGEA3, POSTN, SLC1A6 and TERT; and IGF2, ANXA10, CTSE, CRH, KRT20, MAGEA3, SLC1A6 and TERT.

In a particular embodiment, the third kit of the invention comprises one or more reagents for detecting and/or quantifying the expression level of the IGF2 gene and one or more reagents for detecting and/or quantifying the expression level of 8 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said kit does not consists of reagents for detecting and/or quantifying the expression level of the following gene combination: IGF2, ANXA10, CTSE, CRH, KRT20, MAGEA3, SLC1A6, TERT and MCM10.

In a particular embodiment, the third kit of the invention comprises one or more reagents for detecting and/or quantifying the expression level of the IGF2 gene and one or more reagents for detecting and/or quantifying the expression level of 9 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 10 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 11 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said kit does not consists of reagents for detecting and/or quantifying the expression level of the following gene combination: IGF2, ANXA10, AHNAK2, CTSE, CRH, KLF9, KRT20, MAGEA3, POSTN, PPP1R14D, SLC1A6 and TERT.

In a particular embodiment, the third kit of the invention comprises one or more reagents for detecting and/or quantifying the expression level of the IGF2 gene and one or more reagents for detecting and/or quantifying the expression level of 12 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 13 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes, with the proviso that said kit does not consists of reagents for detecting and/or quantifying the expression level of the following gene combination: IGF2, ANXA10, AHNAK2, CTSE, CRH, KLF9, KRT20, MAGEA3, POSTN, PPP1R14D, SLC1A6, TERT, ASAM and MCM10.

In a particular embodiment, the third kit of the invention comprises one or more reagents for detecting and/or quantifying the expression level of the IGF2 gene and one or more reagents for detecting and/or quantifying the expression level of 14 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 15 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2 gene and one or more reagents for detecting and/or quantifying the expression level of 16 genes selected from the group consisting of the MAGEA3, ANXA10, AHNAK2, CTSE, CRH, KLF9, KRT20, POSTN, PPP1R14D, SLC1A6, TERT, ASAM, MCM10, EBF1, CFH and MMP12 genes.

In a particular embodiment, the third kit of the invention comprises one or more reagents for detecting and/or quantifying the expression level of the IGF2, CRH and KRT20 genes. In a particular embodiment, said kit comprises reagents for detecting and/or quantifying mRNA of the IGF2, CRH and KRT20 genes. In a particular embodiment, said reagents for detecting and/or quantifying mRNA of the IGF2, CRH and KRT20 genes comprise probes which hybridize with cDNA to said mRNAs of IGF2, CRH and KRT20 or pairs of oligonucleotide primers which hybridize with said mRNAs of said IGF2, CRH and KRT20 genes or with said cDNAs to said mRNAs of said IGF2, CRH and KRT20 genes. In another particular embodiment, said reagents for detecting and/or quantifying the expression level of the IGF2, CRH and KRT20 genes comprise antibodies that recognize proteins encoded by said IGF2, CRH and KRT20 genes.

In a particular embodiment, the third kit of the invention comprises one or more reagents for detecting and/or quantifying the expression level of the IGF2, CRH and ANXA10 genes. In a particular embodiment, said kit comprises reagents for detecting and/or quantifying mRNA of the IGF2, CRH and ANXA10 genes. In a particular embodiment, said reagents for detecting and/or quantifying mRNA of the IGF2, CRH and ANXA10 genes comprise probes which hybridize with cDNA to said mRNAs of IGF2, CRH and ANXA10 or pairs of oligonucleotide primers which hybridize with said mRNAs of said IGF2, CRH and ANXA10 genes or with said cDNAs to said mRNAs of said IGF2, CRH and ANXA10 genes. In another particular embodiment, said reagents for detecting and/or quantifying the expression level of the IGF2, CRH and ANXA10 genes comprise antibodies that recognize proteins encoded by said IGF2, CRH and ANXA10 genes.

In a particular embodiment, the third kit of the invention comprises one or more reagents for detecting and/or quantifying the expression level of the IGF2, ANXA10 and KRT20 genes. In a particular embodiment, said kit comprises reagents for detecting and/or quantifying mRNA of the IGF2, ANXA10 and KRT20 genes. In a particular embodiment, said reagents for detecting and/or quantifying mRNA of the IGF2, ANXA10 and KRT20 genes comprise probes which hybridize with cDNA to said mRNAs of IGF2, ANXA10 and KRT20 or pairs of oligonucleotide primers which hybridize with said mRNAs of said IGF2, ANXA10 and KRT20 genes or with said cDNAs to said mRNAs of said IGF2, ANXA10 and KRT20 genes. In another particular embodiment, said reagents for detecting and/or quantifying the expression level of the IGF2, ANXA10 and KRT20 genes comprise antibodies that recognize proteins encoded by said IGF2, ANXA10 and KRT20 genes.

In a particular embodiment, the third kit of the invention comprises one or more reagents for detecting and/or quantifying the expression level of the IGF2, MAGEA3 and KLF9 genes. In a particular embodiment, said kit comprises reagents for detecting and/or quantifying mRNA of the IGF2, MAGEA3 and KLF9 genes. In a particular embodiment, said reagents for detecting and/or quantifying mRNA of the IGF2, MAGEA3 and KLF9 genes comprise probes which hybridize with cDNA to said mRNAs of IGF2, MAGEA3 and KLF9 or pairs of oligonucleotide primers which hybridize with said mRNAs of said IGF2, MAGEA3 and KLF9 genes or with said cDNAs to said mRNAs of said IGF2, MAGEA3 and KLF9 genes. In another particular embodiment, said reagents for detecting and/or quantifying the expression level of the IGF2, MAGEA3 and KLF9 genes comprise antibodies that recognize proteins encoded by said IGF2, MAGEA3 and KLF9 genes.

In a particular embodiment, the third kit of the invention comprises one or more reagents for detecting and/or quantifying the expression level of the IGF2, MAGEA3 and SLC1A6 genes. In a particular embodiment, said kit comprises reagents for detecting and/or quantifying mRNA of the IGF2, MAGEA3 and SLC1A6 genes. In a particular embodiment, said reagents for detecting and/or quantifying mRNA of the IGF2, MAGEA3 and SLC1A6 genes comprise probes which hybridize with cDNA to said mRNAs of IGF2, MAGEA3 and SLC1A6 or pairs of oligonucleotide primers which hybridize with said mRNAs of said IGF2, MAGEA3 and SLC1A6 genes or with said cDNAs to said mRNAs of said IGF2, MAGEA3 and SLC1A6 genes. In another particular embodiment, said reagents for detecting and/or quantifying the expression level of the IGF2, MAGEA3 and SLC1A6 genes comprise antibodies that recognize proteins encoded by said IGF2, MAGEA3 and SLC1A6 genes.

In a particular embodiment, the third kit of the invention comprises one or more reagents for detecting and/or quantifying the expression level of the IGF2, MAGEA3 and CRH genes. In a particular embodiment, said kit comprises reagents for detecting and/or quantifying mRNA of the IGF2, MAGEA3 and CRH genes. In a particular embodiment, said reagents for detecting and/or quantifying mRNA of the IGF2, MAGEA3 and CRH genes comprise probes which hybridize with cDNA to said mRNAs of IGF2, MAGEA3 and CRH or pairs of oligonucleotide primers which hybridize with said mRNAs of said IGF2, MAGEA3 and CRH genes or with said cDNAs to said mRNAs of said IGF2, MAGEA3 and CRH genes. In another particular embodiment, said reagents for detecting and/or quantifying the expression level of the IGF2, MAGEA3 and CRH genes comprise antibodies that recognize proteins encoded by said IGF2, MAGEA3 and CRH genes.

In a particular embodiment, the third kit of the invention comprises one or more reagents for detecting and/or quantifying the expression level of the IGF2, KLF9 and SLC1A6 genes. In a particular embodiment, said kit comprises reagents for detecting and/or quantifying mRNA of the IGF2, KLF9 and SLC1A6 genes. In a particular embodiment, said reagents for detecting and/or quantifying mRNA of the IGF2, KLF9 and SLC1A6 genes comprise probes which hybridize with cDNA to said mRNAs of IGF2, KLF9 and SLC1A6 or pairs of oligonucleotide primers which hybridize with said mRNAs of said IGF2, KLF9 and SLC1A6 genes or with said cDNAs to said mRNAs of said IGF2, KLF9 and SLC1A6 genes. In another particular embodiment, said reagents for detecting and/or quantifying the expression level of the IGF2, KLF9 and SLC1A6 genes comprise antibodies that recognize proteins encoded by said IGF2, KLF9 and SLC1A6 genes.

In a particular embodiment, the third kit of the invention comprises one or more reagents for detecting and/or quantifying the expression level of the IGF2, CRH and SLC1A6 genes. In a particular embodiment, said kit comprises reagents for detecting and/or quantifying mRNA of the IGF2, CRH and SLC1A6 genes. In a particular embodiment, said reagents for detecting and/or quantifying mRNA of the IGF2, CRH and SLC1A6 genes comprise probes which hybridize with cDNA to said mRNAs of IGF2, CRH and SLC1A6 or pairs of oligonucleotide primers which hybridize with said mRNAs of said IGF2, CRH and SLC1A6 genes or with said cDNAs to said mRNAs of said IGF2, CRH and SLC1A6 genes. In another particular embodiment, said reagents for detecting and/or quantifying the expression level of the IGF2, CRH and SLC1A6 genes comprise antibodies that recognize proteins encoded by said IGF2, CRH and SLC1A6 genes.

In a particular embodiment, the third kit of the invention comprises one or more reagents for detecting and/or quantifying the expression level of the IGF2, CRH and KLF9 genes. In a particular embodiment, said kit comprises reagents for detecting and/or quantifying mRNA of the IGF2, CRH and KLF9 genes. In a particular embodiment, said reagents for detecting and/or quantifying mRNA of the IGF2, CRH and KLF9 genes comprise probes which hybridize with cDNA to said mRNAs of IGF2, CRH and KLF9 or pairs of oligonucleotide primers which hybridize with said mRNAs of said IGF2, CRH and KLF9 genes or with said cDNAs to said mRNAs of said IGF2, CRH and KLF9 genes. In another particular embodiment, said reagents for detecting and/or quantifying the expression level of the IGF2, CRH and KLF9 genes comprise antibodies that recognize proteins encoded by said IGF2, CRH and KLF9 genes.

In a particular embodiment, the third kit of the invention comprises one or more reagents for detecting and/or quantifying the expression level of the IGF2, CRH, KLF9 and SLC1A6 genes. In a particular embodiment, said kit comprises reagents for detecting and/or quantifying mRNA of the IGF2, CRH, KLF9 and SLC1A6 genes. In a particular embodiment, said reagents for detecting and/or quantifying mRNA of the IGF2, CRH, KLF9 and SLC1A6 genes comprise probes which hybridize with cDNA to said mRNAs of IGF2, CRH, KLF9 and SLC1A6 or pairs of oligonucleotide primers which hybridize with said mRNAs of said IGF2, CRH, KLF9 and SLC1A6 genes or with said cDNAs to said mRNAs of said IGF2, CRH, KLF9 and SLC1A6 genes. In another particular embodiment, said reagents for detecting and/or quantifying the expression level of the IGF2, CRH, KLF9 and SLC1A6 genes comprise antibodies that recognize proteins encoded by said IGF2, CRH, KLF9 and SLC1A6 genes.

In a particular embodiment, the third kit of the invention comprises one or more reagents for detecting and/or quantifying the expression level of the IGF2, MAGEA3, KLF9 and CRH genes. In a particular embodiment, said kit comprises reagents for detecting and/or quantifying mRNA of the IGF2, MAGEA3, KLF9 and CRH genes. In a particular embodiment, said reagents for detecting and/or quantifying mRNA of the IGF2, MAGEA3, KLF9 and CRH genes comprise probes which hybridize with cDNA to said mRNAs of IGF2, MAGEA3, KLF9 and CRH or pairs of oligonucleotide primers which hybridize with said mRNAs of said IGF2, MAGEA3, KLF9 and CRH genes or with said cDNAs to said mRNAs of said IGF2, MAGEA3, KLF9 and CRH genes. In another particular embodiment, said reagents for detecting and/or quantifying the expression level of the IGF2, MAGEA3, KLF9 and CRH genes comprise antibodies that recognize proteins encoded by said IGF2, MAGEA3, KLF9 and CRH genes.

In a particular embodiment, the third kit of the invention comprises one or more reagents for detecting and/or quantifying the expression level of the IGF2, MAGEA3, CTSE and MMP12 genes. In a particular embodiment, said kit comprises reagents for detecting and/or quantifying mRNA of the IGF2, MAGEA3, CTSE and MMP12 genes. In a particular embodiment, said reagents for detecting and/or quantifying mRNA of the IGF2, MAGEA3, CTSE and MMP12 genes comprise probes which hybridize with cDNA to said mRNAs of IGF2, MAGEA3, CTSE and MMP12 or pairs of oligonucleotide primers which hybridize with said mRNAs of said IGF2, MAGEA3, CTSE and MMP12 genes or with said cDNAs to said mRNAs of said IGF2, MAGEA3, CTSE and MMP12 genes. In another particular embodiment, said reagents for detecting and/or quantifying the expression level of the IGF2, MAGEA3, CTSE and MMP12 genes comprise antibodies that recognize proteins encoded by said IGF2, MAGEA3, CTSE and MMP12 genes.

In a particular embodiment, the third kit of the invention comprises one or more reagents for detecting and/or quantifying the expression level of the IGF2, MAGEA3, CRH, KLF9 and SLC1A6 genes. In a particular embodiment, said kit comprises reagents for detecting and/or quantifying mRNA of the IGF2, MAGEA3, CRH, KLF9 and SLC1A6 genes. In a particular embodiment, said reagents for detecting and/or quantifying mRNA of the IGF2, MAGEA3, CRH, KLF9 and SLC1A6 genes comprise probes which hybridize with cDNA to said mRNAs of IGF2, MAGEA3, CRH, KLF9 and SLC1A6 or pairs of oligonucleotide primers which hybridize with said mRNAs of said IGF2, MAGEA3, CRH, KLF9 and SLC1A6 genes or with said cDNAs to said mRNAs of said IGF2, MAGEA3, CRH, KLF9 and SLC1A6 genes. In another particular embodiment, said reagents for detecting and/or quantifying the expression level of the IGF2, MAGEA3, CRH, KLF9 and SLC1A6 genes comprise antibodies that recognize proteins encoded by said IGF2, MAGEA3, CRH, KLF9 and SLC1A6 genes.

In a particular embodiment, the third kit of the invention comprises one or more reagents for detecting and/or quantifying the expression level of the IGF2, MAGEA3, KLF9, ANHAK2, BFE1 and MMP12 genes. In a particular embodiment, said kit comprises reagents for detecting and/or quantifying mRNA of the IGF2, MAGEA3, KLF9, ANHAK2, BFE1 and MMP12 genes. In a particular embodiment, said reagents for detecting and/or quantifying mRNA of the IGF2, MAGEA3, KLF9, ANHAK2, BFE1 and MMP12 genes comprise probes which hybridize with cDNA to said mRNAs of IGF2, MAGEA3, KLF9, ANHAK2, BFE1 and MMP12 or pairs of oligonucleotide primers which hybridize with said mRNAs of said IGF2, MAGEA3, KLF9, ANHAK2, BFE1 and MMP12 genes or with said cDNAs to said mRNAs of said IGF2, MAGEA3, KLF9, ANHAK2, BFE1 and MMP12 genes. In another particular embodiment, said reagents for detecting and/or quantifying the expression level of the IGF2, MAGEA3, KLF9, ANHAK2, BFE1 and MMP12 genes comprise antibodies that recognize proteins encoded by said IGF2, MAGEA3, KLF9, ANHAK2, BFE1 and MMP12 genes.

In a particular embodiment, the third kit of the invention comprises one or more reagents for detecting and/or quantifying the expression level of the IGF2, MAGEA3, KLF9, PPP1R14D, SLC1A6 and ASAM genes. In a particular embodiment, said kit comprises reagents for detecting and/or quantifying mRNA of the IGF2, MAGEA3, KLF9, PPP1R14D, SLC1A6 and ASAM genes. In a particular embodiment, said reagents for detecting and/or quantifying mRNA of the IGF2, MAGEA3, KLF9, PPP1R14D, SLC1A6 and ASAM genes comprise probes which hybridize with cDNA to said mRNAs of IGF2, MAGEA3, KLF9, PPP1R14D, SLC1A6 and ASAM or pairs of oligonucleotide primers which hybridize with said mRNAs of said IGF2, MAGEA3, KLF9, PPP1R14D, SLC1A6 and ASAM genes or with said cDNAs to said mRNAs of said IGF2, MAGEA3, KLF9, PPP1R14D, SLC1A6 and ASAM genes. In another particular embodiment, said reagents for detecting and/or quantifying the expression level of the IGF2, MAGEA3, KLF9, PPP1R14D, SLC1A6 and ASAM genes comprise antibodies that recognize proteins encoded by said IGF2, MAGEA3, KLF9, PPP1R14D, SLC1A6 and ASAM genes.

In a particular embodiment, the third kit of the invention comprises one or more reagents for detecting and/or quantifying the expression level of the IGF2, MAGEA3, KLF9, PPP1R14D, SLC1A6 and MCM10 genes. In a particular embodiment, said kit comprises reagents for detecting and/or quantifying mRNA of the IGF2, MAGEA3, KLF9, PPP1R14D, SLC1A6 and MCM10 genes. In a particular embodiment, said reagents for detecting and/or quantifying mRNA of the IGF2, MAGEA3, KLF9, PPP1R14D, SLC1A6 and MCM10 genes comprise probes which hybridize with cDNA to said mRNAs of IGF2, MAGEA3, KLF9, PPP1R14D, SLC1A6 and MCM10 or pairs of oligonucleotide primers which hybridize with said mRNAs of said IGF2, MAGEA3, KLF9, PPP1R14D, SLC1A6 and MCM10 genes or with said cDNAs to said mRNAs of said IGF2, MAGEA3, KLF9, PPP1R14D, SLC1A6 and MCM10 genes. In another particular embodiment, said reagents for detecting and/or quantifying the expression level of the IGF2, MAGEA3, KLF9, PPP1R14D, SLC1A6 and MCM10 genes comprise antibodies that recognize proteins encoded by said IGF2, MAGEA3, KLF9, PPP1R14D, SLC1A6 and MCM10 genes.

In a particular embodiment, the third kit of the invention comprises one or more reagents for detecting and/or quantifying the expression level of the IGF2, MAGEA3, CRH, KLF9, SLC1A6, EBF1 and CFH genes. In a particular embodiment, said kit comprises reagents for detecting and/or quantifying mRNA of the IGF2, MAGEA3, CRH, KLF9, SLC1A6, EBF1 and CFH genes. In a particular embodiment, said reagents for detecting and/or quantifying mRNA of the IGF2, MAGEA3, CRH, KLF9, SLC1A6, EBF1 and CFH genes comprise probes which hybridize with cDNA to said mRNAs of IGF2, MAGEA3, CRH, KLF9, SLC1A6, EBF1 and CFH or pairs of oligonucleotide primers which hybridize with said mRNAs of said IGF2, MAGEA3, CRH, KLF9, SLC1A6, EBF1 and CFH genes or with said cDNAs to said mRNAs of said IGF2, MAGEA3, CRH, KLF9, SLC1A6, EBF1 and CFH genes. In another particular embodiment, said reagents for detecting and/or quantifying the expression level of the IGF2, MAGEA3, CRH, KLF9, SLC1A6, EBF1 and CFH genes comprise antibodies that recognize proteins encoded by said IGF2, MAGEA3, CRH, KLF9, SLC1A6, EBF1 and CFH genes.

In a particular embodiment, the third kit of the invention comprises one or more reagents for detecting and/or quantifying the expression level of the IGF2, MAGEA3, CRH, KLF9, PPP1R14D, SLC1A6 and EBF1 genes. In a particular embodiment, said kit comprises reagents for detecting and/or quantifying mRNA of the IGF2, MAGEA3, CRH, KLF9, PPP1R14D, SLC1A6 and EBF1 genes. In a particular embodiment, said reagents for detecting and/or quantifying mRNA of the IGF2, MAGEA3, CRH, KLF9, PPP1R14D, SLC1A6 and EBF1 genes comprise probes which hybridize with cDNA to said mRNAs of IGF2, MAGEA3, CRH, KLF9, PPP1R14D, SLC1A6 and EBF1 or pairs of oligonucleotide primers which hybridize with said mRNAs of said IGF2, MAGEA3, CRH, KLF9, PPP1R14D, SLC1A6 and EBF1 genes or with said cDNAs to said mRNAs of said IGF2, MAGEA3, CRH, KLF9, PPP1R14D, SLC1A6 and EBF1 genes. In another particular embodiment, said reagents for detecting and/or quantifying the expression level of the IGF2, MAGEA3, CRH, KLF9, PPP1R14D, SLC1A6 and EBF1 genes comprise antibodies that recognize proteins encoded by said IGF2, MAGEA3, CRH, KLF9, PPP1R14D, SLC1A6 and EBF1 genes.

In a particular embodiment, the third kit of the invention comprises one or more reagents for detecting and/or quantifying the expression level of the IGF2, MAGEA3, CRH, KLF9, PPP1R14D, SLC1A6, EBF1 and CFH genes. In a particular embodiment, said kit comprises reagents for detecting and/or quantifying mRNA of the IGF2, MAGEA3, CRH, KLF9, PPP1R14D, SLC1A6, EBF1 and CFH genes. In a particular embodiment, said reagents for detecting and/or quantifying mRNA of the IGF2, MAGEA3, CRH, KLF9, PPP1R14D, SLC1A6, EBF1 and CFH genes comprise probes which hybridize with cDNA to said mRNAs of IGF2, MAGEA3, CRH, KLF9, PPP1R14D, SLC1A6, EBF1 and CFH or pairs of oligonucleotide primers which hybridize with said mRNAs of said IGF2, MAGEA3, CRH, KLF9, PPP1R14D, SLC1A6, EBF1 and CFH genes or with said cDNAs to said mRNAs of said IGF2, MAGEA3, CRH, KLF9, PPP1R14D, SLC1A6, EBF1 and CFH genes. In another particular embodiment, said reagents for detecting and/or quantifying the expression level of the IGF2, MAGEA3, CRH, KLF9, PPP1R14D, SLC1A6, EBF1 and CFH genes comprise antibodies that recognize proteins encoded by said IGF2, MAGEA3, CRH, KLF9, PPP1R14D, SLC1A6, EBF1 and CFH genes.

In a particular embodiment, the third kit of the invention comprises one or more reagents for detecting and/or quantifying the expression level of the IGF2, MAGEA3, CRH, PPP1R14D, SLC1A6, EBF1, CFH and MMP12 genes. In a particular embodiment, said kit comprises reagents for detecting and/or quantifying mRNA of the IGF2, MAGEA3, CRH, PPP1R14D, SLC1A6, EBF1, CFH and MMP12 genes. In a particular embodiment, said reagents for detecting and/or quantifying mRNA of the IGF2, MAGEA3, CRH, PPP1R14D, SLC1A6, EBF1, CFH and MMP12 genes comprise probes which hybridize with cDNA to said mRNAs of IGF2, MAGEA3, CRH, PPP1R14D, SLC1A6, EBF1, CFH and MMP12 or pairs of oligonucleotide primers which hybridize with said mRNAs of said IGF2, MAGEA3, CRH, PPP1R14D, SLC1A6, EBF1, CFH and MMP12 genes or with said cDNAs to said mRNAs of said IGF2, MAGEA3, CRH, PPP1R14D, SLC1A6, EBF1 and MMP12 genes. In another particular embodiment, said reagents for detecting and/or quantifying the expression level of the IGF2, MAGEA3, CRH, PPP1R14D, SLC1A6, EBF1, CFH and MMP12 genes comprise antibodies that recognize proteins encoded by said IGF2, MAGEA3, CRH, PPP1R14D, SLC1A6, EBF1, CFH and MMP12 genes.

In a particular embodiment, the third kit of the invention comprises one or more reagents for detecting and/or quantifying the expression level of the IGF2, MAGEA3, CRH, KLF9, PPP1R14D, SLC1A6, EBF1, CFH and MMP12 genes. In a particular embodiment, said kit comprises reagents for detecting and/or quantifying mRNA of the IGF2, MAGEA3, CRH, KLF9, PPP1R14D, SLC1A6, EBF1, CFH and MMP12 genes. In a particular embodiment, said reagents for detecting and/or quantifying mRNA of the IGF2, MAGEA3, CRH, KLF9, PPP1R14D, SLC1A6, EBF1, CFH and MMP12 genes comprise probes which hybridize with cDNA to said mRNAs of IGF2, MAGEA3, CRH, KLF9, PPP1R14D, SLC1A6, EBF1, CFH and MMP12 or pairs of oligonucleotide primers which hybridize with said mRNAs of said IGF2, MAGEA3, CRH, KLF9, PPP1R14D, SLC1A6, EBF1, CFH and MMP12 genes or with said cDNAs to said mRNAs of said IGF2, MAGEA3, CRH, KLF9, PPP1R14D, SLC1A6, EBF1, CFH and MMP12 genes. In another particular embodiment, said reagents for detecting and/or quantifying the expression level of the IGF2, MAGEA3, CRH, KLF9, PPP1R14D, SLC1A6, EBF1, CFH and MMP12 genes comprise antibodies that recognize proteins encoded by said IGF2, MAGEA3, CRH, KLF9, PPP1R14D, SLC1A6, EBF1, CFH and MMP12 genes.

In a particular embodiment, the third kit of the invention comprises one or more reagents for detecting and/or quantifying the expression level of the IGF2, MAGEA3, POSTN, TERT, ASAM, MCM10, EBF1, CFH and MMP12 genes. In a particular embodiment, said kit comprises reagents for detecting and/or quantifying mRNA of the IGF2, MAGEA3, POSTN, TERT, ASAM, MCM10, EBF1, CFH and MMP12 genes. In a particular embodiment, said reagents for detecting and/or quantifying mRNA of the IGF2, MAGEA3, POSTN, TERT, ASAM, MCM10, EBF1, CFH and MMP12 genes comprise probes which hybridize with cDNA to said mRNAs of IGF2, MAGEA3, POSTN, TERT, ASAM, MCM10, EBF1, CFH and MMP12 or pairs of oligonucleotide primers which hybridize with said mRNAs of said IGF2, MAGEA3, POSTN, TERT, ASAM, MCM10, EBF1, CFH and MMP12 genes or with said cDNAs to said mRNAs of said IGF2, MAGEA3, POSTN, TERT, ASAM, MCM10, EBF1, CFH and MMP12 genes. In another particular embodiment, said reagents for detecting and/or quantifying the expression level of the IGF2, MAGEA3, POSTN, TERT, ASAM, MCM10, EBF1, CFH and MMP12 genes comprise antibodies that recognize proteins encoded by said IGF2, MAGEA3, POSTN, TERT, ASAM, MCM10, EBF1, CFH and MMP12 genes.

In a particular embodiment, the third kit of the invention comprises one or more reagents for detecting and/or quantifying the expression level of the IGF2, MAGEA3, CRH, KLF9, SLC1A6, POSTN, EBF1, CFH, MCM10 and MMP12 genes. In a particular embodiment, said kit comprises reagents for detecting and/or quantifying mRNA of the IGF2, MAGEA3, CRH, KLF9, SLC1A6, POSTN, EBF1, CFH, MCM10 and MMP12 genes. In a particular embodiment, said reagents for detecting and/or quantifying mRNA of the IGF2, MAGEA3, CRH, KLF9, SLC1A6, POSTN, EBF1, CFH, MCM10 and MMP12 genes comprise probes which hybridize with cDNA to said mRNAs of IGF2, MAGEA3, CRH, KLF9, SLC1A6, POSTN, EBF1, CFH, MCM10 and MMP12 or pairs of oligonucleotide primers which hybridize with said mRNAs of said IGF2, MAGEA3, CRH, KLF9, SLC1A6, POSTN, EBF1, CFH, MCM10 and MMP12 genes or with said cDNAs to said mRNAs of said IGF2, MAGEA3, CRH, KLF9, SLC1A6, POSTN, EBF1, CFH, MCM10 and MMP12 genes. In another particular embodiment, said reagents for detecting and/or quantifying the expression level of the IGF2, MAGEA3, CRH, KLF9, SLC1A6, POSTN, EBF1, CFH, MCM10 and MMP12 genes comprise antibodies that recognize proteins encoded by said IGF2, MAGEA3, CRH, KLF9, SLC1A6, POSTN, EBF1, CFH, MCM10 and MMP12 genes.

In a particular embodiment, said third kit of the invention further comprises a reagent for detecting and/or quantifying the expression level of one or more of the genes selected from the group consisting of the FOXM1, KIF20A, MELK and CDK1 genes and any combination thereof. To that end, said kit will incorporate the necessary reagents depending on the gene or genes the expression level/levels of which is/are to be quantified, such as, for example, reagents for detecting and/or quantifying mRNA of one or more of the FOXM1, KIF20A, MELK and CDK1 genes, such as, for example, probes which hybridize with cDNA to said mRNAs of FOXM1, KIF20A, MELK and/or CDK1 or pairs of oligonucleotide primers which hybridize with said mRNAs of said FOXM1, KIF20A, MELK and/or CDK1 genes, or with said cDNAs to said mRNAs of said FOXM1, KIF20A, MELK and/or CDK1 genes. In another particular embodiment, said reagents for detecting and/or quantifying the expression level of the FOXM1, KIF20A, MELK and/or CDK1 genes comprise antibodies that recognize proteins encoded by said FOXM1, KIF20A, MELK and/or CDK1 genes.

In a particular embodiment, the third kit of the invention comprises one or more reagents for detecting and/or quantifying the expression level of the IGF2, MAGEA3, CRH, KLF9, SLC1A6, POSTN, EBF1, CFH, MCM10, MMP12, TERT, FOXM1, KIF20A, MELK and CDK1 genes. In a particular embodiment, said kit comprises reagents for detecting and/or quantifying mRNA of the IGF2, MAGEA3, CRH, KLF9, SLC1A6, POSTN, EBF1, CFH, MCM10, MMP12, TERT, FOXM1, KIF20A, MELK and CDK1 genes. In a particular embodiment, said reagents for detecting and/or quantifying mRNA of the IGF2, MAGEA3, CRH, KLF9, SLC1A6, POSTN, EBF1, CFH, MCM10, MMP12, TERT, FOXM1, KIF20A, MELK and CDK1 genes comprise probes which hybridize with cDNA to said mRNAs of IGF2, MAGEA3, CRH, KLF9, SLC1A6, POSTN, EBF1, CFH, MCM10, MMP12, TERT, FOXM1, KIF20A, MELK and CDK1 or pairs of oligonucleotide primers which hybridize with said mRNAs of said IGF2, MAGEA3, CRH, KLF9, SLC1A6, POSTN, EBF1, CFH, MCM10, MMP12, TERT, FOXM1, KIF20A, MELK and CDK1 genes or with said cDNAs to said mRNAs of said IGF2, MAGEA3, CRH, KLF9, SLC1A6, POSTN, EBF1, CFH, MCM10, MMP12, TERT, FOXM1, KIF20A, MELK and CDK1 genes. In another particular embodiment, said reagents for detecting and/or quantifying the expression level of the IGF2, MAGEA3, CRH, KLF9, SLC1A6, POSTN, EBF1, CFH, MCM10, MMP12, TERT, FOXM1, KIF20A, MELK and CDK1 genes comprise antibodies that recognize proteins encoded by said IGF2, MAGEA3, CRH, KLF9, SLC1A6, POSTN, EBF1, CFH, MCM10, MMP12, TERT, FOXM1, KIF20A, MELK and CDK1 genes.

In another aspect, the invention relates to the use of any of the kits of the invention for bladder cancer diagnosis.

Further, as the skilled person in the art may understand, the teachings of the invention can also be applied to monitor or follow up the periodic or repetitive diagnosis along the time in patients who have previously suffered bladder cancer and who have been treated but who should still be under vigilance due to the high risk of recurrence of this kind of cancer. Typically, patients are monitored at different time intervals ranging usually between 3 months and 1 year from the last treatment.

Therefore, in another aspect, the invention relates to the use of any of the kits of the invention for bladder cancer monitoring. The particulars of the kits of the invention have been previously mentioned and are included herein by reference.

The following examples serve to illustrate the invention and must not be considered as limiting of the scope thereof. To carry out said examples, the materials and methods described therein were used.

EXAMPLE 1

Clinical Validation of the Model Formed by the Combination of 12 Genes for Bladder Cancer Diagnosis This example was carried out to validate the precision of a 12-gene model [IGF2, ANXA10, AHNAK2, CTSE, CRH, KLF9, KRT20, MAGEA3, POSTN, PPP1R14D, SLC1A6 and TERT] developed in an independent patient and control cohort.

Materials and Methods

Samples and Patients

The urine samples from 239 consecutive bladder cancer patients and the control samples which were used in this example were prospectively collected between February 2009 and January 2010 in Hospital Clinic of Barcelona. All the individuals included in the study were previously informed of the objectives of the study and signed the informed consent form. This validation study is derived from a global project previously approved by the Hospital Ethics Committee.

Fourteen of the 239 urine samples collected were excluded from the study given that less than 10 ng of RNA were obtained. On the other hand, those samples which did not comply with the RNA quality criteria were excluded (n=18, see below in the section relating to "Data Analysis"). Finally, 207 urine samples were analyzed in this validation study: 96 samples from patients subjected to surgical transurethral resection (TUR) due to having a primary or recurrent bladder tumor and a histologically confirmed tumor (72 men, 24 women, mean age 71.8 years) and 111 urine samples from control patients with non-neoplastic urological diseases and healthy controls (47 men, 64 women, mean age 58.3 years) (Table 1). The grade and the stage of the tumors were determined according to the World Health Organization (WHO) classification [Lopez-Beltran A et al. Tumours of the Urinary System. In: Eble J N, Sauter G, Epstein J I, Sesterhenn I A, editors. Pathology and Genetics of Tumours of the Urinary System and Male Genital Organs. World Health Organization Classification of Tumours. Lyon: IARC Press, 2004. p. 89-157] and the TNM classification [Sobin L H & Wittekind C H. TNM Classification of Malignant Tumours. International Union Against Cancer., ed. 6th. New York: John Wiley & Sons; 2002].

The tumors were classified according to their risk in three categories:

low-risk non-muscle invasive bladder cancer (NMIBC, Ta and T1 low grade without associated CIS);

high-risk NMIBC (low grade Ta or T1 with associated CIS, high grade Ta or T1 and Tis); and muscle-invasive bladder cancer (MIBC, T2, T3, T4 and LG HG with or without associated CIS).

The clinical-pathological characteristics of the patients and controls included in the study are shown in Table 1.

TABLE 1

Clinical-pathological characteristics of the patients and controls included in the study

| | | Training set (N = 211) | Validation set (N = 207) |
|---|---|---|---|
| Tumor samples (urine) | | | |
| Tis | | 2 | 4 |
| Ta LG | −CIS | 39 | 25 |
| | +CIS | — | 1 |
| Ta HG | −CIS | 9 | 5 |
| | +CIS | 1 | 3 |
| Ta Gx | −CIS | — | 1 |
| T1 LG | −CIS | 5 | 5 |
| | +CIS | — | 1 |
| T1 HG | −CIS | 11 | 24 |
| | +CIS | 4 | 5 |
| T2, T3, T4 LG | −CIS | — | 1 |
| T2, T3, T4 HG | −CIS | 22 | 18 |
| | +CIS | 4 | 2 |
| Tx LG | −CIS | — | 1 |
| Total tumors | | 97 | 96 |
| Control samples (urine) | | | |
| Benign prostate hyperplasia | | 29 | 14 |
| Urolithiasis | | 22 | 33 |
| Incontinence | | 9 | 14 |
| Urethral stricture | | 13 | 4 |
| Urinary tract infection | | 7 | 1 |

TABLE 1-continued

Clinical-pathological characteristics of the patients
and controls included in the study

|  | Training set (N = 211) | Validation set (N = 207) |
|---|---|---|
| Healthy | 25 | 33 |
| Others | 9 | 12 |
| Total controls | 114 | 111 |
| Total | 211 | 207 |

CIS: In situ carcinoma
GX: Grade not determined
HG: High grade
LG: Low grade
Ta: Non-invasive papillary carcinoma or papillary carcinoma confined to the mucosa
Tis: In situ carcinoma. Flat superficial tumor that does not invade the lamina propria.
Tx: Primary tumor
T1: Tumor that invades the sub-epithelial connective tissue or that invades the lamina propria.
T2: Tumor that invades the bladder muscle layer.
T3: Tumor that invades beyond the muscle layer or that invades the prevesical fat.
T4: Tumor that invades structures adjacent to the urinary bladder.

Processing the Urine Sample

The urine samples were collected before subjecting the patient to TUR in the case group or during their study in the Urology Service in the case of the controls. Between 50 and 100 ml of urine were collected in containers prepared with RNA stabilizing agent (1/25 volumes of 0.5 M ethylenediaminetetraacetic acid (EDTA), pH 8.0), which were stored at 4° C. and processed over the following 24 hours. The samples were centrifuged at 1000×g for 10 minutes at 4° C. Next, the supernatant was discarded and the cell pellets were resuspended in 1 ml of TRIzol (Invitrogen, Carlsbad, Calif., USA) and frozen at −80° C. until the subsequent total RNA extraction.

The total RNA was extracted from the urine samples homogenized in the TRIzol reagent following the supplier's instructions (Invitrogen, Carlsbad, Calif., USA). The RNA obtained was then quantified by means of a spectrophotometer (NanoDrop ND-1000).

Quantitative PCR in TaqMan Arrays

Ten to 500 ng of total RNA obtained from the urine samples, according to availability, were used to obtain complementary DNA (cDNA) by means of the TaqMan RNA Reverse Transcription Kit® (Applied Biosystems) following the supplier's instructions, except that the final volume of the reaction was 25 µl. A total of 6.25 µl of each cDNA were pre-amplified by means of a multiplex reaction that contained 45 target genes plus 2 endogenous controls (Table 2), using the TaqMan®PreAmp Master Mix kit (Applied Biosystems) following the supplier's recommendations, except that the final reaction volume was 25 µl. Finally, 5 µl of the pre-amplified and diluted cDNA were mixed with 50 µl of 2× TaqMan Universal PCR Mastermix (AB) in a final volume of 100 µl and were amplified by means of TaqMan arrays in singleplex reactions using the manufacturer's recommendations (Applied Biosystems).

TABLE 2

List of the 45 target genes and 2 endogenous controls analyzed in the study

| Gene symbol | Assay ID (Applied Biosystems) | Gene name |
|---|---|---|
| TMBIM6 | Hs00162661_m1 | transmembrane BAX inhibitor motif containing 6 |
| PPIA | Hs99999904_m1 | peptidylprolyl isomerase A (cyclophilin A) |
| GUSB | Hs99999908_m1 | glucuronidase, beta |
| ANLN | Hs00218803_m1 | anillin, actin binding protein |
| ANXA10 | Hs00200464_m1 | annexin A10 |
| ASAM | Hs00293345_m1 | adipocyte-specific adhesion molecule |
| ASPM | Hs00411505_m1 | asp (abnormal spindle) homolog, microcephaly associated (Drosophila) |
| BIRC5- | Hs00153353_m1 | baculoviral IAP repeat-containing 5 |
| AHNAK2 | Hs00746838_s1 | AHNAK nucleoprotein 2 |
| CCNA2 | Hs00153138_m1 | cyclin A2 |
| CDK1 | Hs00364293_m1 | cyclin-dependent kinase 1 |
| CDC20 | Hs00415851_g1 | cell division cycle 20 homolog (S. cerevisiae) |
| NUF2 | Hs00230097_m1 | NUF2, NDC80 kinetochore complex component, homolog (S. cerevisiae) |
| CDH1 | Hs00170423_m1 | cadherin 1, type 1, E-cadherin (epithelial) |
| CENPF | Hs00193201_m1 | centromere protein F, 350/400 ka (mitosin) |
| CFH | Hs00164830_m1 | complement factor H |
| CRH | Hs00174941_m1 | corticotropin releasing hormone |
| CTSE | Hs00157213_m1 | cathepsin E |
| DLGAP5 | Hs00207323_m1 | discs, large (Drosophila) homolog-associated protein 5 |
| EBF1 | Hs00395513_m1 | early B-cell factor 1 |
| FGFR3 | Hs00179829_m1 | fibroblast growth factor receptor 3 |
| FOXM1 | Hs00153543_m1 | forkhead box M1 |
| IGF2 | Hs00171254_m1 | insulin-like growth factor 2 (somatomedin A) |
| IQGAP3 | Hs00603642_m1 | IQ motif containing GTPase activating protein 3 |
| KIF20A | Hs00194882_m1 | kinesin family member 20A |
| KIF2C | Hs00199232_m1 | kinesin family member 2C |
| KIF4A | Hs00602211_g1 | kinesin family member 4A |
| KLF9 | Hs00230918_m1 | Kruppel-like factor 9 |
| KRT14 | Hs00265033_m1 | keratin 14 |
| KRT20 | Hs00300643_m1 | keratin 20 |
| MAGEA3 | Hs00366532_m1 | melanoma antigen family A, 3 |
| MAGEA9; MAGEA9B | Hs00245619_s1 | melanoma antigen family A, 9; melanoma antigen family A, 9B |
| MCM10 | Hs00218560_m1 | minichromosome maintenance complex component 10 |
| MDK | Hs00171064_m1 | midkine (neurite growth-promoting factor 2) |
| MELK | Hs00207681_m1 | maternal embryonic leucine zipper kinase |
| MKI67 | Hs00606991_m1 | antigen identified by monoclonal antibody Ki-67 |
| MMP12 | Hs00159178_m1 | matrix metallopeptidase 12 (macrophage elastase) |
| NEK2 | Hs00601227_mH | NIMA (never in mitosis gene a)-related kinase 2 |
| POLQ | Hs00198196_m1 | polymerase (DNA directed), theta |
| POSTN | Hs00170815_m1 | periostin, osteoblast specific factor |

TABLE 2-continued

List of the 45 target genes and 2 endogenous controls analyzed in the study

| Gene symbol | Assay ID (Applied Biosystems) | Gene name |
|---|---|---|
| PPP1R14D | Hs00214613_m1 | protein phosphatase 1, regulatory (inhibitor) subunit 14D |
| SLC1A6 | Hs00192604_m1 | solute carrier family 1 (high affinity aspartate/glutamate transporter), member 6 |
| TERT | Hs00162669_m1 | telomerase reverse transcriptase |
| TOP2A | Hs00172214_m1 | topoisomerase (DNA) II alpha 170 kDa |
| TPX2 | Hs00201616_m1 | TPX2, microtubule-associated, homolog (*Xenopus laevis*) |
| TRIP13 | Hs00188500_m1 | thyroid hormone receptor interactor 13 |
| VEGFA | Hs00900054_m1 | vascular endothelial growth factor A |

The 45 target genes (including the combination of 12 genes of the model under study) and the 2 endogenous controls analyzed in a previous study performed by the same inventors [Mengual L et al. Gene expression signature in urine for diagnosing and assessing aggressiveness of bladder urothelial carcinoma. Clin Cancer Res 2010; 16:2624-33] were analyzed in all the samples of the validation study for the purpose of evaluating the possibility of improving the model by adding or eliminating a gene.

Data Analysis

The quantitative PCR data were processed with the SDS 2.4 and Enterprise programs (Applied Biosystems). The threshold and baseline for each gene were established automatically. To enable comparison with previous data extracted with a manual threshold, the threshold of the previously analyzed samples was automatically re-analyzed.

The data was normalized with the geometric mean of the cycle threshold or CT of the 2 reference genes (GUSB and PPIA). For the purpose of assuring reliability of the results, the samples with a higher GUSB CT value ±3 mean SD (standard deviation) of the GUSB CT of the entire group of patients and controls, it was considered that they had low RNA quality and were excluded from the analysis (n=18 samples, 12 controls and 6 tumors; GUSB CT=24.62; GUSB CT range=22.4-30.27).

The relative expression levels of the target genes in a sample were expressed as ΔCT $$\Delta CT = CT_{reference\ gene\ mean} - CT_{target\ gene}$$

Genes with CT values greater than 35 were considered as poorly expressed and their ΔCT was attributed to the minimum ΔCT value for that gene. Logistic regression was used to evaluate the performance of the combination of 12 genes in the independent sample validation set. Multidimensional scaling plots were constructed to view the dissimilarity between the control and tumor groups according to the expression of the 12 genes. R software was used for all the calculations and to construct heat maps and scatter plots. The ROC curve was used to calculate model sensitivity and specificity.

The ROC curves were made with DiagnosisMed (CRAN.R-project.org/package=DiagnosisMed) and Proc package. All the calculations were performed using R software.

Results 207 urine samples were used to validate the group consisting of the combination of 12 genes [IGF2, ANXA10, AHNAK2, CTSE, CRH, KLF9, KRT20, MAGEA3, POSTN, PPP1R14D, SLC1A6 and TERT] for non-invasive bladder cancer diagnosis described above. Signature sensitivity (SN) and specificity (SP) in the validation set were 80% and 86%, respectively (AUC: 0.914) (FIG. 1A). As in the training set, SN increases as the tumor risk increases, being lower in low-risk NMIBC (containing 15 of the 19 incorrectly classified tumors samples) and reaches 100% in MIBC (FIG. 1B). Concerning SP, 15 of the 111 control samples were incorrectly classified by the genetic signature of 12 genes in the validation set. The overall precision for the diagnosis in the independent validation set was 84%.

EXAMPLE 2

Identification of a Second Generation of Genetic Signatures for Bladder Cancer Diagnosis For the purpose of mitigating to the extent possible the over-training of the model due to the use of a reduced number of samples, all the analyzed urine samples [samples used for training of the model plus the samples used for validation (Example 1)] were grouped together to obtain a larger set of training samples. Samples with a higher GUSB CT value ±2 mean SD of the GUSB CT of the entire group of patients and controls of the preceding validation set were excluded from the analysis (n=14 samples, 11 control samples and 3 tumor samples). Therefore, the new enlarged set of samples finally contained 404 samples (211+193). This enlarged set of samples was used both to re-evaluate the preceding 12-gene model and to generate new combinations of genes which have given rise to some genetic signatures provided by this invention for bladder cancer diagnosis with greater precision and a smaller number of genes.

Forward stepwise logistic regression was used to that end to determine if there were other combinations of genes with greater precision and a smaller number of genes for non-invasive UC diagnosis [Hastie T J & Pregibon D. Generalized linear models. In: Chambers J M, Hastie T J, editors. Statistical Models in S. Wadsworth & Brooks/Cole, 1992].

The ROC curves were made with DiagnosisMed (CRAN.R-project.org/package=DiagnosisMed) and Proc package [Robin X et al. pROC: an open-source package for R and S+to analyze and compare ROC curves. BMC Bioinformatics 2011; 12:77]. All the calculations were performed using R software. The "globaltest algorithm" [Goeman J J et al. A global test for groups of genes: testing association with a clinical outcome. Bioinformatics 2004; 20:93-9] of the Bioconductor software package was used to analyze the association of the genes studied with diagnostic prediction and aggressiveness.

The evaluation of the 12-gene diagnostic model re-evaluated (identified as "GS_D12" in Table 4) in the enlarged training set of urine samples reached a precision of 88% (AUC 0.944) in the discrimination between the control urines and UC patient urines (Table 3).

TABLE 3

Diagnostic performance of the genetic signatures identified in the enlarged training population (N = 404)

| Genetic signature | SN (%) | SP (%) | PPV (%) | NPV (%) | RE (%) | AUC | Cut-off value |
|---|---|---|---|---|---|---|---|
| GS_D12 | 85.86 | 90.14 | 88.65 | 87.67 | 11.88 | 0.944 | 0.4392224 |
| GS_D10 | 86.39 | 90.14 | 88.71 | 88.07 | 11.63 | 0.949 | 0.4358558 |
| GS_D5 | 84.29 | 90.61 | 88.95 | 86.55 | 12.38 | 0.941 | 0.4227185 |
| GS_D3(1) | 77.49 | 90.14 | 87.57 | 81.7 | 15.84 | 0.921 | 0.5409575 |
| GS_D3(2) | 78.53 | 90.14 | 87.72 | 82.40 | 15.35 | 0.920 | 0.5380129 |
| GS_D3(3) | 68.59 | 90.14 | 86.18 | 76.19 | 20.05 | 0.901 | 0.9047405 |
| GS_D2(1) | 78.53 | 90.14 | 87.72 | 82.4 | 15.35 | 0.913 | 0.4920999 |
| GS_D2(2) | 78.53 | 90.14 | 87.72 | 82.4 | 15.35 | 0.920 | 0.5340469 |
| GS_D2(3) | 68.59 | 90.14 | 86.18 | 76.19 | 20.05 | 0.890 | 0.5826062 |
| GS_D2(4) | 69.11 | 90.14 | 86.27 | 76.49 | 19.8 | 0.900 | 0.6207051 |
| DS_D1 | 68.59 | 90.61 | 86.75 | 76.28 | 19.8 | 0.883 | 0.5908347 |

SN: sensitivity;
SP: specificity;
PPV: positive predictive value;
NPV: negative predictive value;
RE: Relative error;
AUC: area under the curve Various combinations of genes that were extremely precise for UC diagnosis were found. Out of all of them, 2 combinations of genes that contained 5 and 10 genes (identified as "GS_D5" and "GS_D10, respectively, in Table 4) were selected. It should be pointed out that the 3 identified genetic combinations (GS_D12, GS_D5 and GS_D10) share 5 markers (IGF2, CRH, KLF9, MAGEA3 and SLC1A6).

TABLE 4

Genes making up each of the genetic signatures

| Gene symbol | GS_D12 | GS_D10 | GS_D5 | GS_D3(1) | GS_D3(2) | GS_D3(3) | GS_D2(1) | GS_D2(2) | GS_D2(3) | GS_D2(4) | GS_D1 |
|---|---|---|---|---|---|---|---|---|---|---|---|
| IGF2 | X | X | X | X | X | X | X | X | X | X | X |
| MAGEA3 | X | X | X | | | | X | | | | |
| CRH | X | X | X | X | X | | | X | | | |
| KLF9 | X | X | X | | | | | | | | |
| SLC1A6 | X | X | X | | | | | | | | |
| POSTN | X | X | | | | | | | | | |
| TERT | X | | | | | | | | | | |
| AHNAK2 | X | | | | | | | | | | |
| ANXA10 | X | | | | X | X | | | X | | |
| CTSE | X | | | | | | | | | | |
| KRT20 | X | | | X | | X | | | | X | |
| PPP1R14D | X | | | | | | | | | | |
| EBF1 | | X | | | | | | | | | |
| CFH | | X | | | | | | | | | |
| MCM10 | | X | | | | | | | | | |
| MMP12 | | X | | | | | | | | | |

Next, the 5 genes that shared the 3 gene signatures were evaluated in further detail to discover the importance of each gene in the signature, determining that:

the combination of 2 genes (GS_D2(1)) [IGF2 and MAGEA3] was extremely precise for bladder cancer diagnosis (Table 3), being complementary to one another; and the IGF2 gene is capable by itself of discriminating between tumor and control samples; nevertheless, adding MAGEA3 greatly increases sensitivity in high-risk tumors.

Finally, given that IGF2 is the gene which by itself provides the most diagnostic information, its diagnostic performance (GS_D1) was evaluated together with the diagnostic performance of other gene signatures [GS_D10, GS_D5, GS_D3 and the four GS_D2 signatures, GS_D2(1), GS_D2(2), GS_D2(3) and GS_D2(4)] in an independent patient and control cohort (Example 3).

EXAMPLE 3

Clinical Validation of the Set of GS_D12, GS_D10, GS_D5, GS_D2 and GS_D1 Signatures in an Independent Cohort Materials and Methods Samples and Patients The GS 12, GS_D10, GS_D5, GS_D3(1), GS_D3(2), GS_D3(1), GS_D2(1), GS_D2(2), GS_D2(3), GS_D2(4) and GS_D1 genetic signatures (Table 4) were validated in an independent patient and control cohort. 790 urine samples were prospectively collected in 5 European centers [Hospital Clínic (Barcelona, Spain), Fundació Puigvert (Barcelona, Spain), Hospital Virgen del Rocío (Seville, Spain), The Radboud University Nijmegen Medical Centre (Nijmegen, Netherlands) and Medical University of Vienna (Vienna, Austria)] from February 2009 to July 2010.

These samples correspond to 370 bladder cancer patients and 420 controls. Out of the 790 subjects included in the study, 147 (17%) were excluded because they were considered screening failures and 118 samples (14%) were also excluded due to technical problems (while collecting the sample or during its analysis). Finally, 525 individuals (216 bladder cancer patients and 309 controls) were included in the study. The clinical and histopathological variables of the patients included in the study are included in Table 5. Tumor grade and stage were determined according to WHO and TNM criteria, respectively.

TABLE 5

Clinical-pathological characteristics of the subjects included in the multicenter validation study

|  | HOSPITAL CLINIC | FUNDACIO PUIGVERT | VIRGEN DEL ROCIO | UNIVERSITY OF VIENNA | RADBOUD UNIVERSITY NIJMEGEN |
|---|---|---|---|---|---|
| N | 59 | 115 | 22 | 14 | 6 |
| MEAN AGE (RANGE) | 72 (51-88) | 74 (38-90) | 65 (45-83) | 72 (59-84) | 65 (30-83) |
| STAGE |  |  |  |  |  |
| Ta | 20 | 71 | 8 | 7 | 4 |
| T1 | 26 | 19 | 11 | 4 | 2 |
| ≥T2 | 10 | 23 | 2 | 3 | 0 |
| GRADE |  |  |  |  |  |
| LG | 21 | 44 | 14 | 8 | 2 |
| HG | 37 | 70 | 7 | 6 | 4 |

HG: High grade
LG: Low grade
Ta: Non-invasive papillary carcinoma or papillary carcinoma confined to the mucosa
T1: Tumor that invades the sub-epithelial connective tissue or that invades the lamina propria.
T2: Tumor that invades the bladder muscle layer.

Clinical Validation

Sample collection and processing, as well as sample analysis, were performed in exactly the same manner as in the training set (Example 1).

The samples were collected and processed until adding the Trizol reagent in the different centers and sent to the reference center for RNA extraction and analysis.

Logistic regression was used to evaluate the performance of the different signatures in the validation set. The probability of each sample being a control or tumor sample was calculated using the data from the training set. The ROC curve was used to determine sensitivity (SN) and specificity (SP) of the 12 models in the validation set, in comparison with the enlarged training set (n=404), after adjusting for age and sex.

The ROC curves were made with DiagnosisMed (CRAN.R-project.org/package=DiagnosisMed) and Proc package [Robin X et al. pROC: an open-source package for R and S+to analyze and compare ROC curves. BMC Bioinformatics 2011; 12:77]. All the calculations were performed using R software.

The AUC for each diagnostic signature varied slightly between the enlarged training set and the validation sets (Table 6).

TABLE 6

Diagnostic performance of the genetic signatures in the validation population (n = 525)

| Genetic signature | SN (%) | SP (%) | PPV (%) | NPV (%) | RE (%) | AUC | Cut-off value |
|---|---|---|---|---|---|---|---|
| GS_D12 | 78.7 | 93.2 | 89.01 | 86.23 | 12.76 | 0.905 | 0.4392224 |
| GS_D10 | 79.63 | 93.53 | 89.58 | 86.79 | 12.19 | 0.908 | 0.4358558 |
| GS_D5 | 79.17 | 91.59 | 86.8 | 86.28 | 13.52 | 0.903 | 0.4227185 |
| GS_D3(1) | 75.93 | 90.94 | 85.42 | 83.38 | 15.24 | 0.895 | 0.5409575 |
| GS_D3(2) | 75.00 | 91.26 | 85.71 | 83.93 | 15.43 | 0.893 | 0.5380129 |
| GS_D3(3) | 75.93 | 91.91 | 86.77 | 84.52 | 14.67 | 0.905 | 0.9047405 |
| GS_D2(1) | 81.48 | 91.26 | 86.7 | 87.58 | 12.76 | 0.918 | 0.4920999 |
| GS_D2(2) | 75.46 | 90.94 | 85.34 | 84.13 | 15.43 | 0.894 | 0.5340469 |
| GS_D2(3) | 75.46 | 90.94 | 85.34 | 84.13 | 15.43 | 0.902 | 0.5826062 |

TABLE 6-continued

Diagnostic performance of the genetic signatures in the validation population (n = 525)

| Genetic signature | SN (%) | SP (%) | PPV (%) | NPV (%) | RE (%) | AUC | Cut-off value |
|---|---|---|---|---|---|---|---|
| GS_D2(4) | 76.39 | 92.23 | 87.30 | 84.82 | 14.29 | 0.907 | 0.6207051 |
| DS_D1 | 76.85 | 91.26 | 86.01 | 84.94 | 14.67 | 0.907 | 0.5908347 |

SN: sensitivity;
SP: specificity;
PPV: positive predictive value;
NPV: negative predictive value;
RE: Relative error;
AUC: area under the curve The results obtained clearly show that the genetic signature that provided the highest diagnostic performance was GS_D10 (AUC 0.908; 87.81% precision). Even still, the GS_D2(1) genetic signature reaches very high precision values (AUC 0.918; 87.24% precision). Finally, the non-invasive UC diagnosis based on only one gene, GS_DS1, reaches an 85.33% precision with an AUC of 0.907.

EXAMPLE 4

Differential Expression of the Target Genes with Significant Differences

The changes in the expression levels of those target genes the differences of which between the control and tumor samples were considered more significant based on the expression results obtained in the microarray, specifically IGF2, ANXA10, AHNAK2, CTSE, CRH, KLF9, KRT20, MAGEA3, POSTN, PPP1R14D, SLC1A6, TERT, EBF1, CFH, MCM10 and MMP12, were corroborated by means of quantitative real-time RT-PCR.

cDNA synthesis from the RNA samples and subsequent cDNA amplification were carried out by means of the Taqman RNA Reverse Transcription Kit® (Applied Biosystems), as indicated in the Materials and Methods section. The reverse transcription was carried out by means of a cycle at 25° C. for 10 minutes, followed by a cycle at 37° C. for 2 hours and a cycle at 85° C. for 5 seconds. cDNA pre-amplification was carried out under the following conditions: a cycle for 10 minutes at 95° C. followed by 14 cycles for 15 seconds at 95° C., and 4 minutes at 60° C. The quantitative PCR conditions were: 1 cycle for 2 minutes at 50° C., a cycle for 10 minutes at 95° C. and 40 cycles for 15 seconds at 95° C. and 1 minute at 60° C.

The results obtained are shown in Table 7.

TABLE 7

Magnitude of the change/differential expression

| Gene symbol | No. of times (diagnosis) |
|---|---|
| IGF2 | 30.0311 |
| MAGEA3 | 13.4155 |
| CRH | 114.9314 |
| KLF9 | −1.4277 |
| SLC1A6 | 37.1548 |
| POSTN | 1.3794 |
| TERT | 4.7496 |
| AHNAK2 | −1.3208 |
| ANXA10 | 10.9467 |
| CTSE | 6.7450 |
| KRT20 | 12.5117 |
| PPP1R14D | 4.6107 |
| EBF1 | −2.2139 |
| CFH | −1.1621 |
| MCM10 | 1.5803 |
| MMP12 | 1.6804 |

The "−" sign indicates that the expression of the gene in the tumor sample is less than the expression of the gene in a non-tumor sample.

What is claimed is:

1. A method for diagnosing a subject who suffers bladder cancer, the method consisting of:
   obtaining a urine sample from said subject;
   determining the expression level of the IGF2 gene and the expression level of a second gene, wherein said second gene is selected from the group consisting of the MAGEA3, ANXA10, CTSE, CRH, KRT20, SLC1A6, TERT, MCM10, EBF1, CFH and MMP12 genes in the urine sample from said subject;
   comparing the expression level of said genes in said sample with their reference values;
   wherein an expression level of the IGF2 gene in the sample from the subject greater than the reference value for said gene; and
   wherein an altered expression level of said second gene in the sample from said subject when compared to the reference value for said gene, wherein said altered expression level is:
      an increased expression level of the MAGEA3, ANXA10, CTSE, CRH, KRT20, SLC1A6, TERT, MCM10 or MMP12 genes, or
      a decreased expression level of the EBF1 or CFH genes,
      are indicative that said subject is likely to suffer from bladder cancer; and
   subjecting the subject to an endoscopic procedure to confirm that the subject suffers bladder cancer.

2. A method for treating a subject who suffers bladder cancer, the method consisting of:
   obtaining a urine sample from said subject;
   determining the expression level of the IGF2 gene and the expression level of a second gene, wherein said second gene is selected from the group consisting of the MAGEA3, ANXA10, CTSE, CRH, KRT20, SLC1A6, TERT, MCM10, EBF1, CFH and MMP12 genes in the urine sample from said subject;
   comparing the expression level of said genes in said sample with their reference values;
   wherein an expression level of the IGF2 gene in the sample from the subject greater than the reference value for said gene; and
   wherein an altered expression level of said second gene in the sample from said subject when compared to the reference value for said gene, wherein said altered expression level is:
      an increased expression level of the MAGEA3, ANXA10, CTSE, CRH, KRT20, SLC1A6, TERT, MCM10 or MMP12 genes, or
      a decreased expression level of the EBF1 or CFH genes,
      are indicative that said subject suffers bladder cancer; and
   administering a transurethral resection (TUR) to the subject if the subject is diagnosed as suffering bladder cancer, said subject benefiting from administering said therapy.

3. A kit selected from the group consisting of:
   a kit consisting of a reagent for detecting and/or quantifying the expression level of a combination of genes consisting of the IGF2 gene and a second gene selected from the group consisting of the MAGEA3, ANXA10, CTSE, CRH, KRT20, SLC1A6, TERT, MCM10, EBF1, CFH and MMP12 genes;
   a kit comprising a reagent for detecting and/or quantifying the expression level of a combination of genes comprising the IGF2 gene and at least two genes selected from the group consisting of the MAGEA3, ANXA10, CTSE, CRH, KRT20, SLC1A6, TERT, MCM10, EBF1, CFH, MMP12 genes and any combination thereof, with the proviso that said combination is not any of the following combinations:
      ANXA10, AHNAK2, CTSE, CRH, KLF9 KRT20, MAGEA3, POSTN, PPP1R14D, SLC1A6, TERT, ASAM, and MCM10;
      ANXA10, AHNAK2, CTSE, CRH, KLF9 KRT20, MAGEA3, POSTN, PPP1R14D, SLC1A6 and TERT;
      ANXA10, CRH, KRT20, MAGEA3, POSTN, SLC1A6 and TERT;
      ANXA10, CTSE, CRH, KRT20, MAGEA3, SLC1A6, TERT and MCM10; or
      ANXA10, CTSE, CRH, KRT20, MAGEA3, SLC1A6 and TERT; and
   a kit consisting of a reagent for detecting and/or quantifying the expression level of a combination of genes consisting of the IGF2, MAGEA3, CRH, KLF9, POSTN, SLC1A6, MCM10, EBF1, CFH and MMP12 genes.

4. A method for diagnosing a subject who suffers bladder cancer, the method consisting of:
   obtaining a urine sample from said subject;
   determining the expression level of the IGF2 gene and the expression level of the MAGEA3, CRH, KLF9, POSTN, SLC1A6, MCM10, EBF1, CFH and MMP12 genes in the urine sample from said subject;
   comparing the expression level of said genes in said sample with their reference values;
   wherein an expression level of the IGF2 gene in the sample from the subject greater than the reference value for said gene; and wherein an altered expression level of said second gene in the sample from said subject when compared to the reference value for said gene, wherein said altered expression level is:
  an increased expression level of the MAGEA3, CRH, POSTN, SLC1A6, MCM10 or MMP12 genes, or
  a decreased expression level of the KLF9, EBF1 or CFH genes,
  are indicative that said subject is likely to suffer from bladder cancer; and
subjecting the subject to an endoscopic procedure to confirm that the subject suffers bladder cancer.

5. A method for treating a subject who suffers bladder cancer, the method consisting of:
  obtaining a urine sample from said subject;
  determining the expression level of the IGF2 gene and the expression level of the MAGEA3, CRH, KLF9, POSTN, SLC1A6, MCM10, EBF1, CFH and MMP12 genes in the urine sample from said subject;
  comparing the expression level of said genes in said sample with their reference values;
  wherein an expression level of the IGF2 gene in the sample from the subject greater than the reference value for said gene; and
  wherein an altered expression level of said second gene in the sample from said subject when compared to the reference value for said gene, wherein said altered expression level is:
    an increased expression level of the MAGEA3, CRH, POSTN, SLC1A6, MCM10 or MMP12 genes, or
    a decreased expression level of the KLF9, EBF1 or CFH genes,
    are indicative that said subject suffers bladder cancer; and
  administering a transurethral resection (TUR) to the subject if the subject is diagnosed as suffering bladder cancer and said subject will benefit from the administration of said therapy.

6. A method for diagnosing a subject who suffers bladder cancer, the method comprising:
  a) obtaining a urine sample from said subject;
  b) determining the expression level of each of the genes present in a combination of genes comprising the IGF2 gene, and at least two genes selected from the group consisting of the MAGEA3, ANXA10, CTSE, CRH, KRT20, SLC1A6, TERT, MCM10, EBF1, CFH and MMP12 genes and any combination thereof in a sample from said subject, with the proviso that said combination of genes is not any of the following combinations:
    ANXA10, AHNAK2, CTSE, CRH, KLF9, KRT20, MAGEA3, POSTN, PPP1R14D, SLC1A6, TERT, ASAM and MCM10;
    ANXA10, AHNAK2, CTSE, CRH, KLF9, KRT20, MAGEA3, POSTN, PPP1R14D, SLC1A6 and TERT;
    ANXA10, CRH, KRT20, MAGEA3, POSTN, SLC1A6 and TERT;
    ANXA10, CTSE, CRH, KRT20, MAGEA3, SLC1A6, TERT and MCM10; or
    ANXA10, CTSE, CRH, KRT20, MAGEA3, SLC1A6 and TERT;
  c) comparing the expression level of said genes in said sample with their reference values;
  wherein:
    an expression level of the IGF2, MAGEA3, ANXA10, CTSE, CRH, KRT20, SLC1A6, TERT, MCM10 and MMP12 genes in the sample from the subject greater than the reference values for each of said genes, and
    an expression level of the EBF1 and CFH genes in the sample from the subject less than the reference values for each of said genes,
  are indicative that said subject is likely to suffer from bladder cancer; and
  d) subjecting the subject to an endoscopic procedure to confirm that the subject suffers bladder cancer.

* * * * *